US006861405B2

(12) United States Patent
Desir et al.

(10) Patent No.: US 6,861,405 B2
(45) Date of Patent: Mar. 1, 2005

(54) COMPOSITIONS AND METHODS RELATING TO GLUCOSE METABOLISM, WEIGHT CONTROL, AND FOOD INTAKE

(75) Inventors: Gary Desir, Woodbridge, CT (US); Jianchao Xu, Bethany, CT (US); Pandelakis A. Koni, Martinez, GA (US); Leonard Kaczmarek, Guilford, CT (US); Richard A. Flavell, Guilford, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 10/167,528

(22) Filed: Jun. 11, 2002

(65) Prior Publication Data

US 2003/0032595 A1 Feb. 13, 2003

Related U.S. Application Data

(60) Provisional application No. 60/297,547, filed on Jun. 12, 2001.

(51) Int. Cl.$^7$ .............................................. A61K 38/17
(52) U.S. Cl. ......................................................... 514/12
(58) Field of Search ........................................... 514/12

(56) References Cited

U.S. PATENT DOCUMENTS

2002/0165237 A1 * 11/2002 Fryburg et al.

OTHER PUBLICATIONS

Breum et al., Metabolizm, V. 44, No. 12, Dec. 1995, pp. 1570–1576.*
Li et al. Brain Res., 781 (1998) 121–128.*
Aiyar et al. American Journal of Physiology 265 (6 Part 1): pC1571–C1578 (1993).*
Arkett et al., 1994, Receptors Channels 2:281–293.
Attali et al., 1992, FEBS Lett., 303:229–232.
Beeton et al., 2001, Proc. Nat. Acad. Sci. USA 98:13942–13947.
Bowlby et al., 1997, J. Gen Physiol 110:601–610.
Breum et al., 1995, Metabolism 44:1570–1576.
Bruning et al., 2000, Science 289:2122–2125.
Choi et al., 1999, Journal of Pharmacology & Experimental Therapeutics 291:1–6.
Chung et al., 1997, J. Membr. Biol. 156: 73–85.
Cline et al., 1999, N. Engl. J. Med. 341:240–246.
Coleman et al., 1978, Diabetologia 14:141–148.
Dal Ponte et al., 1998, Metabolism 47:982–987.
Deng et al., 2002, Am. J. Hum. Genet. 70:1138–1151.
Fadool et al., 1998, J. Neurosci 18:6126–6137.
Fadool et al., 2000, J. Neurophysiol. 83: 2332–2348.
Frougel et al., 2001, Exp. Biol. Med. 226:991–996.
Ghanshani et al., 2000, J. Biol. Chem. 275:37137–37149.
Hajduch et al., 1999, J. Biol. Chem. 274:13563–13568.
Jacob et al., 2000, Mol. Hum. Reprod. 6:303–313.
Kalman et al., 1998, J. Biol. Chem. 49: 32697–32707.
Komarova et al., 2001, Curr. Pharm. Des. 7:637–654.
Koo et al., 1999, Cell Immunol. 197:99–107.
Kourrich et al., 2001, Behav. Brain Res. 120:35–46.
Lang et al., 1999, Herz. 24: 232–235.
Levite et al., 2000, J. Exp. Med. 191:1167–1176.
MacDonald et al., 2001, Mol. Endocrinol. 15:1423–1435.
Madeja et al., 2000, Neuropharmacology 39:202–210.
Miki et al., 2001, Nat. Neurosci 4:507–512.
Mourre et al., 1999, J. Pharm. Exp. Ther. 291:943–952.
Potter van Loon et al., 1992, Int. J. Obes. Rela. Metab,. Disord. 16:79–85.
Robe et al., 2000, Br. J. Pharmacol 131:1275–1284.
Veh et al., 1995, Eur. J. Neurosci. 7:2189–2205.
Warntges et al., 2002, Pflugers Arch. 443: 617–624.
Yao et al, 1996, J. Clin. Invest. 97:2525–2533.
Yeung et al., 1999, Br. J. Pharmacol 128:1609–1615.
Yu et al., 1999, Am. J. Physiol 277:E259–E267.
Zhang et al., 1994, Nature 372:425–432.

* cited by examiner

*Primary Examiner*—Robert A. Wax
(74) *Attorney, Agent, or Firm*—Morgan, Lewis & Bockius, LLP

(57) ABSTRACT

The present invention relates to weight control, control of body fat and food intake, and provides useful methods for treating, inter alia, obesity, diabetes and insulin insensitivity, and conditions, diseases, and disorders relating thereto. The invention also relates to methods of identifying useful compounds relating to weight loss, food intake, diabetes, and obesity, among other things, based on the discovery that inhibiting Kv1.3 activity mediates decreased food intake, weight loss, decreased body fat, increase glucose uptake, and increased insulin sensitivity, among other things.

12 Claims, 12 Drawing Sheets

COMPOSITIONS AND METHODS RELATING TO GLUCOSE METABOLISM, WEIGHT CONTROL, AND FOOD INTAKE

CROSS REFERENCE TO RELATED APPLICATIONS

This application is entitled to priority, pursuant to 35 U.S.C. §119(e), to U.S. provisional patent application No. 60/297,547, which was filed on Jun. 12, 2001.

STATEMENT REGARDING FEDERALLY SUPPORTED RESEARCH OR DEVELOPMENT

This research was supported in part by U.S. Government funds (Veteran Administration Merit Review Award and National Institutes of Health Grant Number DK48105B and K08DK02917) and the U.S. Government may therefore have certain rights in the invention.

BACKGROUND OF THE INVENTION

Obesity

Obesity is arguably the greatest public health threat in modern Western society, and it is an increasing threat throughout the world. A recent Surgeon General's report underscores the impact of obesity on human health. According to the report, approximately 61% of adults in the United States are overweight or obese, and the prevalence of overweight children and adolescents has doubled in the past two decades. The estimated economic burden of obesity to the United States alone is about $117 billion annually, and obesity is associated with an estimated 300,000 deaths per year. Further, numerous diseases have been correlated to obesity: Heart disease, certain types of cancer, sleep apnea, asthma, arthritis, pregnancy complications, depression and type II diabetes mellitus are all associated with excess weight.

In light of the health dangers attributed to obesity, many treatments, both pharmacological and non-pharmacological, have been developed to combat this enormous problem. Non-pharmacological approaches include diet, exercise and surgical intervention. While a well-balanced diet consumed in moderation coupled with regular physical activity is the most easily applied method of controlling or losing weight, the aforementioned facts indicate that this method has not reversed the trend towards increasing obesity. Reasons for lack of exercise may include cardiovascular problems or physical imparities that limit aerobic exercise, or lack of discipline, motivation, or time. Thus, behavior modification methods have proven unsuccessful in reversing the trend towards increasing obesity.

A variety of methods of treatment for obesity have been employed to address this pressing health issue. For instance, surgical intervention has been employed in conditions where obesity manifests as a real and immediate danger to a person's health. Previous surgical techniques to treat obesity included intragastric balloons and ileojejunal bypass surgery, but they often led to severe malnutrition, intestinal obstruction, and associated liver or renal failure. The art has progressed to biliopancreatic bypass, gastric bypass, and gastric partitioning (stomach-stapling) surgeries. While an improvement over older methods, these techniques are invasive surgical procedures with well-known and significant inherent risks and complications, and have not been in use long enough to be completely evaluated for long term safety.

Pharmacological methods to control weight have targeted a spectrum of physiological processes. Central nervous system (CNS) appetite suppressants interact with catecholaminergic receptors in the brain stem or regulate available serotonin levels. Drawbacks to these agents include possible addiction and numerous side effects including nervousness, insomnia, drowsiness, depression, nausea and lassitude.

Another class of pharmacologic agents for weight control promotes malabsorption of fats and carbohydrates through inhibition of digestive enzymes. Amylase, glycosidase and lipase inhibitors have been isolated from bacterial or fungal sources, and have been used to prevent the absorption of fats and carbohydrates in the digestive tract. A major problem with these agents is that it is virtually impossible to maintain physiological levels of these inhibitors that can effectively inhibit gastrointestinal enzymes, and therefore absorption. Additionally, the use of these inhibitors often leads to compensatory cravings for other foods. As an example, subjects taking a lipase inhibitor will often consume more carbohydrates to compensate for the loss of fat absorption in the diet, thereby negating any weight control benefits.

Another type of weight control agents is non-caloric, non-nutritive dietary substitutes, including saccharine, aspartame, and sucrose polyester (a fat substitute). The sucrose substitutes, saccharine and aspartame, have been linked to hyperphagia in order to compensate for the loss of calories from naturally occurring sucrose, and therefore may not help control weight. Furthermore, these are only sugar substitutes, and do not impact the role of fat consumed in the diet. Sucrose polyester is a sucrose bound to varying numbers and lengths of fatty acid chains. The size and complexity of the fatty acid chains prevent it from being absorbed, but also binds many fat-soluble vitamins, leading to vitamin deficiencies. Further, sucrose polyester has been associated with severe and unpredictable gastrointestinal instability and fecal incontinence.

In addition to the methods directed towards controlling obesity using pharmacological and surgical methods, a great deal of research has been conducted to elucidate the underlying genetic and biochemical mechanisms of obesity. Many human genes have been linked directly to obesity (Zhang et al., 1994, Nature 372:425–432; Deng et al., 2002, Am. J. Hum. Genet. 70:1138–1151), or to obesity susceptibility (Frougel and Boutin, 2001, Exp. Biol. Med. 226:991–996). Additionally, many of the genes involved in obesity have also been implicated in diabetes mellitus (Coleman et al., 1978, Diabetologia 14:141–148)

Diabetes Mellitus

Diabetes mellitus is a devastating metabolic disease characterized by the presence of chronically elevated blood glucose, abnormal glucose, protein, and lipid metabolism due to either insulin deficiency or resistance. The World Health Organization classifies patients as either having insulin-dependent diabetes mellitus (Type I, IDDM) or non-insulin-dependent diabetes mellitus (Type II, NIDDM). Type I patients do not produce sufficient amounts of insulin to maintain normal glucose metabolism. Type II patients exhibit various degrees of insulin resistance and typically have increased insulin levels early in the disease. Insulin levels may decrease as pancreatic secretion falls, presumably because of chronic over-stimulation.

Diabetes affects over 14 million in the United States (90% Type II and 10% type I) and accounts for approximately 15% of all health care expenditure. It is the leading cause of adult blindness in people 20 to 74 years old, of non-traumatic lower extremity amputation, and of end-stage renal disease. Since the hallmark of type I diabetes is insulin deficiency, patients are treated with insulin. In contrast, patients with Type II diabetes frequently do not require exogenous insulin, since insulin production is often adequate. Instead, treatment of Type II diabetes usually begins with diet and lifestyle modifications. If after an adequate trial of diet and lifestyle modifications, fasting hyperglycemia persists, then an oral hypoglycemic agent is used. Finally, insulin may be added if adequate glucose control cannot be achieved with oral agents.

There are two broad classes of oral hypoglycemic agents. Sulfonylureas inhibit ATP-regulated potassium channels present in the pancreatic β cells and facilitate endogenous insulin secretion. The second class of agent, exemplified by rosiglitazone, ameliorates insulin resistance. They are believed to be preferable to sulfonylureas since they specifically reverse an essential feature of Type II diabetes i.e. insulin resistance. Drugs that improve insulin sensitivity have great potential for use in the treatment of Type II diabetes.

Kv1.3

Of the genes implicated in obesity susceptibility, a few are involved in insulin related signaling, especially in the central nervous and endocrine systems. Knockout mice lacking the neuronal insulin receptor (JR) exhibited normal neuronal survival and brain development, but developed mild insulin resistance, diet-sensitive obesity, and weighed approximately 15% more than controls (Bruning et al., 2000, Science 289:2122–2125), suggesting a role for insulin in the CNS and a role for CNS insulin in obesity. The downstream signaling pathway initiated by the insulin-IR interaction remains ill defined, but proteins containing Src-homology-3 and Src-homology domains, as well as the voltage-gated potassium channel protein Kv1.3, have been implicated as insulin receptor substrates (Fadool et al., 2000, J. Neurophysiol. 83:2332–2348).

Kv1.3 belongs to the Shaker family of voltage regulate potassium channels. Kv1.3 is expressed in the central nervous system, kidney, lymphocytes, liver, testis, spermatozoa, osteoclasts, heart and skeletal muscle (Yao et al, 1996, J. Clin. Invest. 97:2525–2533; Cahalan et al., 1991, Curr. Topics. Memb. 39:357–394; Ghanshani et al., 2000, J. Biol. Chem. 275;37137–37149; Levite et al., 2000, J. Exp. Med. 191:1167–1176; Mourre et al., 1999, J. Pharmacol. Exp. Ther. 291:943–952; Jacob et al., 2000, Mol. Hum. Reprod. 6:303–313, Arkett et al., 1994, Receptors Channels 2:281–293; Komarova et al., 2001, Curr. Pharm. Des. 7:637–654). Analysis of the primary amino acid sequence of Kv1.3 revealed that the protein contains six-transmembrane domains, a consensus protein kinase C site, a tyrosine kinase phosphorylation site, and a glycosylation site. The protein kinase C site is conserved amongst all Shaker potassium channels, and phosphorylation of that site appears to down regulate potassium channel activity (Chandy et al., 1995, In: Handbook of Receptors and Channels, C.R.C. Press, Inc., Boca Raton, Fla.). Recent data has also suggested that Kv1.3 activity is downregulated by tyrosine phosphorylation through the action of insulin (Fadool et al., 2000, J. Neurophysiol. 83:2332–2348).

Many studies have concluded that Kv1.3 is important in thymocyte activity (DeCoursey et al., 1985, J. Neuroimmunol. 10:71–95; Matteson and Deutch, 1984, Nature 307:468–471). Additionally, it has been reported that inhibition of Kv1.3 channels with selective toxins (correolide, margatoxin, and derivatives) has an immunosuppressive function (Koo et al., 1999, Cell Immunol. 197:99–107). Finally, inhibition of Kv1.3 with margatoxin or similar compounds has been shown to ameliorate experimental autoimmune encephalomyelitis, a model for multiple sclerosis, by suppressing the T-cell response to myelin basic protein (Beeton et al., 2001, Proc. Nat. Acad. Sci. USA 98:13942–13947); inhibition of Kv1.3 in rats increases associative learning and memory (Kourrich et al., 2001, Behav. Brain Res. 120:35–46). However, the physiological role of Kv1.3 in the CNS and other physiological processes remains poorly defined.

Despite the current status of obesity and obesity-associated disease as a world-wide crisis, there are no effective and sustainable treatments for this disease. The treatment of diabetes still requires further refinement, especially the discovery of drugs that increase insulin sensitivity. Therefore, there is a long felt need for a safe and effective method to treat obesity and associated disorders, such as diabetes. The present invention meets this need.

BRIEF SUMMARY OF THE INVENTION

The invention includes a method for inducing weight loss in an animal. The method comprises administering to an animal a voltage-gated potassium channel Kv1.3 inhibiting amount of a Kv1.3 inhibitor, thereby inducing weight loss in the animal.

In one aspect, the Kv1.3 inhibitor is selected from the group consisting of a ribozyme, an antisense nucleic acid, an antibody, a peptide and a chemical compound.

In another aspect, the chemical compound is selected from the group consisting of 4-aminopyridine, H-89 (N-[2-(p-bromocinnamylamino)ethyl]-5-isoquinolinesulfonamide), Hstx1, ShK-Dap$^{22}$, short scorpion toxin family (bmtx1, bmktx, bmtx2, bmp02, neurotoxin, tstx-k alpha, margatoxin, noxiustoxin, maurotoxin, charybdotoxin, scyllatoxin, agitoxin, chlorootoxin, butantoxin, toxin ts kappa, toxin I5a, toxin analog, toxin analog P01, OSK1 toxin, kaliotoxin, LQ2 toxin, pandinus toxin), clotrimazole, paxilline, stichodactyla toxin, melatonin, tetraethylammonium chloride, α-dendrotoxin, β-dendrotoxin, tityustoxin-Kα, noxiustoxin, agitoxin-2, κ-conotoxin, hanatoxin, hongotoxin, correolide, WIN 17317-3 (1-Benzyl-7-chloro-4-n-propylimino-1,4-dihydroquiniline), UK78282 (4-[(Diphenylmethoxy)methyl]-1-[3-(4-methyoxyphenyl) propyl]-piperidine), CP 339818 hydrochloride (N-[1-(Phenylmethyl)-4(1H)-quinolinylidene]-1pentanamine hydrochloride), iberiotoxin, verapamil, nifedipine, fluxetime, a serotonin uptake inhibitor, and a serotonin agonist.

In one aspect, the short scorpion toxin is selected from the group consisting of bmtx1, bmktx, bmtx2, bmp02, neurotoxin, tstx-k alpha, margatoxin, noxiustoxin, maurotoxin, charybdotoxin, scyllatoxin, agitoxin, chlorootoxin, butantoxin, toxin ts kappa, toxin I5a, toxin analog, toxin analog P01, OSK1 toxin, kaliotoxin, LQ2 toxin, and pandinus toxin.

The invention includes a method for decreasing body fat in an animal. The method comprises administering a Kv1.3 inhibiting amount of a Kv1.3 inhibitor to the animal, thereby decreasing body fat in the animal.

In one aspect, the animal is selected from the group consisting of a bird, a rodent, and a mammal, and further wherein the mammal is selected from the group consisting of a cow, a pig, a sheep, a buffalo, a beefalo, a bison, a deer, a goat, and a human.

The invention also includes a method for increasing insulin sensitivity in an animal. The method comprises administering a Kv1.3 inhibiting amount of a Kv1.3 inhibitor to an animal, thereby increasing insulin sensitivity in the animal.

The invention includes a method for decreasing food intake in an animal, the method comprising administering a Kv1.3 inhibiting amount of a Kv1.3 inhibitor to an animal, thereby decreasing food intake in the animal.

The invention further includes a method for affecting appetite in an animal. The method comprises administering a Kv1.3 inhibiting amount of a Kv1.3 inhibitor to an animal, thereby affecting appetite in the animal.

The invention includes a method for treating obesity in an animal. The method comprises administering a Kv1.3 inhibiting amount of a Kv1.3 inhibitor to an animal, thereby treating obesity in the animal.

The invention also includes a method for preventing obesity in an animal. The method comprises administering a Kv1.3 inhibiting amount of a Kv1.3 inhibitor to an animal, thereby preventing obesity in the animal.

The invention includes a method for treating a glucose-metabolism disease or disorder in an animal. The method comprises administering a Kv1.3 inhibiting amount of a Kv1.3 inhibitor to an animal, thereby treating a glucose-metabolism disorder in the animal.

In one aspect, the glucose-metabolism disease or disorder is selected from the group consisting of obesity, diabetes, insulin resistance, glucose intolerance, hyerinsulinemia, Syndrome X, hypercholesterolemia, hyperlipoproteinemia, hypertriglyceridemia, atherosclerosis, and diabetic renal disease.

The invention includes a method of producing a transgenic non-human mammal having a decreased body fat content compared with the body fat content of an otherwise identical non-transgenic mammal. The method comprises producing a transgenic non-human mammal lacking Kv1.3 activity, thereby producing a transgenic non-human mammal having decreased body fat content compared with the body fat content of the otherwise identical non-transgenic mammal.

The invention also includes a method for affecting physical activity in an animal. The method comprises administering a Kv1.3 inhibiting amount of a Kv1.3 inhibitor to an animal, thereby affecting physical activity in the animal.

The invention includes a method for affecting metabolic rate in an animal. The method comprises administering a Kv1.3 inhibiting amount of a Kv1.3 inhibitor to an animal, thereby affecting metabolic rate in the animal.

The invention also includes a method of identifying a compound useful for treatment of obesity in an animal. The method comprises administering a compound to an animal and comparing the level of Kv1.3 activity in the animal with the level of Kv1.3 activity in an otherwise identical animal to which the compound is not administered. A lower level of Kv1.3 activity in the animal to which the compound was administered compared with the level of Kv1.3 activity in the otherwise identical animal is an indication that the compound is useful for treatment of obesity, thereby identifying a compound useful for treatment of obesity in the animal. In one aspect, the invention includes a compound identified by this method.

The invention includes a method of identifying a compound useful for treatment of obesity. The method comprises contacting a cell with a compound and comparing the level of Kv1.3 activity in the cell contacted with the compound with the level of Kv1.3 activity in an otherwise identical cell not contacted with the compound, wherein a lower level of Kv1.3 activity in the cell contacted with the compound compared with the level of Kv1.3 activity in the otherwise identical cell not contacted with the compound is an indication that the compound is useful for treatment of obesity, thereby identifying a compound useful for treatment of obesity.

In one aspect, the cell is selected from the group consisting of a skeletal muscle cell, a fat cell, a liver cell, a brain cell, a kidney cell, and a pancreas cell.

In one aspect, the skeletal muscle cell is a rat L6 cell.

The invention includes a method of identifying a compound that inhibits Kv1.3 activity in an animal. The method comprises administering a compound to an animal and comparing the level of Kv1.3 activity in the animal with the level of Kv1.3 activity in the animal prior to administration of the compound, wherein the Kv1.3 activity is selected from the group consisting of increased cellular glucose uptake, decreased food intake, decreased percent body fat, increased insulin sensitivity, increased physical activity, and increased metabolic rate, wherein a decrease in the level of Kv1.3 activity in the animal compared with the level of Kv1.3 activity in the animal prior to administration of the compound is an indication that the compound inhibits Kv1.3, thereby identifying a compound that inhibits Kv1.3 activity in the mammal.

In one aspect, the invention includes a compound identified by this method.

The invention includes a kit for treating obesity in an animal. The kit comprises an effective amount of a Kv1.3 inhibitor, and further comprises an applicator and an instructional material for the use of the kit.

The invention also includes a kit for decreasing body fat in an animal. The kit comprising an effective amount of a Kv1.3 inhibitor, and further comprises an applicator and an instructional material for the use of the kit.

The invention includes a kit for inducing weight loss in an animal. The kit comprises an effective amount of a Kv1.3 inhibitor, and further comprises an applicator and an instructional material for the use of the kit.

The invention further comprises a kit for increasing insulin sensitivity in an animal. The kit comprises an effective amount of a Kv1.3 inhibitor, and further comprises an applicator and an instructional material for the use of the kit.

The invention includes a kit for decreasing food intake in an animal. The kit comprises an effective amount of a Kv1.3 inhibitor, and further comprises an applicator and an instructional material for the use of the kit.

The invention also includes a kit for preventing obesity in an animal. The kit comprises an effective amount of a Kv1.3 inhibitor, and further comprises an applicator and an instructional material for the use of the kit.

In one aspect, inhibitor is selected from the group consisting of 4-aminopyridine, H-89 (N-[2-(p-bromocinnamylamino)ethyl]-5-isoquinolinesulfonamide), Hstx1, ShK-Dap$^{22}$, a short scorpion toxin, clotrimazole, paxilline, stichodactyla toxin, melatonin, tetraethylammonium chloride, α-dendrotoxin, β-dendrotoxin, tityustoxin-Kα, noxiustoxin, agitoxin-2, κ-conotoxin, hanatoxin, hongotoxin, correolide, WIN 17317-3 (1-Benzyl-7-chloro-4-n-propylimino-1,4-dihydroquiniline), UK78282 (4-[(Diphenylmethoxy)methyl]-1-[3-(4-methyoxyphenyl)propyl]-piperidine), CP 339818 hydrochloride (N-[1-(Phenylmethyl)-4(1H)-quinolinylidene]-1 pentanamine hydrochloride), iberiotoxin, verapamil, nifedipine, fluxetime, a serotonin uptake inhibitor, and a serotonin agonist.

In one aspect, the short scorpion toxin is selected from the group consisting of bmtx1, bmkktx, bmtx2, bmp02, neurotoxin, tstx-k alpha, margatoxin, noxiustoxin, maurotoxin, charybdotoxin, scyllatoxin, agitoxin, chlorootoxin, butantoxin, toxin ts kappa, toxin I5a, toxin analog, toxin analog P01, OSK1 toxin, kaliotoxin, LQ2 toxin, and pandinus toxin.

The invention includes a kit for treating a glucose-metabolism disease or disorder in an animal. The kit comprises an effective amount of a Kv1.3 inhibitor, and further comprises an applicator and an instructional material for the use of the kit.

In one aspect, the inhibitor is selected from the group consisting of 4-aminopyridine, H-89 (N-[2-(p-bromocinnamylamino)ethyl]-5-isoquinolinesulfonamide), Hstx1, ShK-Dap$^{22}$, a short scorpion toxin, clotrimazole, paxilline, stichodactyla toxin, melatonin, tetraethylammonium chloride, α-dendrotoxin, β-dendrotoxin, tityustoxin-Kα, noxiustoxin, agitoxin-2, κ-conotoxin, hanatoxin, hongotoxin, correolide, WIN 17317-3 (1-Benzyl-7-chloro-4-n-propylimino-1,4-dihydroquiniline), UK78282 (4-[(Diphenylmethoxy)methyl]-1-[3-(4-methyoxyphenyl) propyl]-piperidine), CP 339818 hydrochloride (N-[1-(Phenylmethyl)-4(1H)-quinolinylidene]-1 pentanamine hydrochloride), iberiotoxin, verapamil, nifedipine, fluxetime, a serotonin uptake inhibitor, and a serotonin agonist.

The invention also includes a kit for affecting appetite in an animal. The kit comprises an effective amount of a Kv1.3 inhibitor, and further comprises an applicator and an instructional material for the use of the kit.

The invention includes a kit for affecting physical activity in an animal. The kit comprises an effective amount of a Kv1.3 inhibitor, and further comprises an applicator and an instructional material for the use of the kit.

The invention includes a kit for affecting metabolic rate in an animal. The kit comprises an effective amount of a Kv1.3 inhibitor, and further comprises an applicator and an instructional material for the use of the kit.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 3, comprising FIG. 3A depicts the targeting construct used to delete the promoter region and the 5' third of the coding region and incorporate a Bam HI (B) site into the construct for screening. Other endonuclease sites indicated are HindIII (H) and ScaI (S). FIG. 3B depicts genomic DNA amplified by the polymerase chain reaction (PCR) using Kv1.3 specific primers (5' primer ATACTTCGACCCGCTCCGCAATGA, SEQ ID NO:1, 3' primer GCAGAAGATGACAATG-GAGATGAG, SEQ ID NO:2) denaturing at 94° C. for 1 minute, annealing at 55° C. for 2 minutes, and extension at 68° C. for 3 minutes, 35 cycles. A band of the expected size (340 bp) was detected by Southern blotting using an internal in wild type but not in Kv1.3 (−/−) mice. FIG. 3C depicts an image of Kv1.3 protein as assayed by Western Blot. Homogenates were prepared from liver, skeletal muscle, kidney, and brain of Kv1.3 (−/−) or Kv1.3 (+/+) mice. Protein (10 μg) was resolved by 10% SDS-PAGE and transferred to a nitrocellulose membrane, which was probed with a rabbit anti-human Kv1.3 polyclonal antibody (1:200) (Alomone, Israel). The control lane is a Kv1.3 fusion protein provided by the manufacturer as a positive control. A band of the expected size (68–72 kDa) was detected in Kv1.3 (+/+) but not Kv1.3 (−/−).

FIG. 6, comprising FIG. 6A depicts the fasting and non-fasting plasma insulin levels of Kv1.3 (−/−) mice and wild type controls. FIG. 6 B is a graph depicting fasting blood glucose levels in age-matched (2 month old) Kv1.3 (−/−) and wild type control mice.

DETAILED DESCRIPTION OF THE INVENTION

Figure 1:
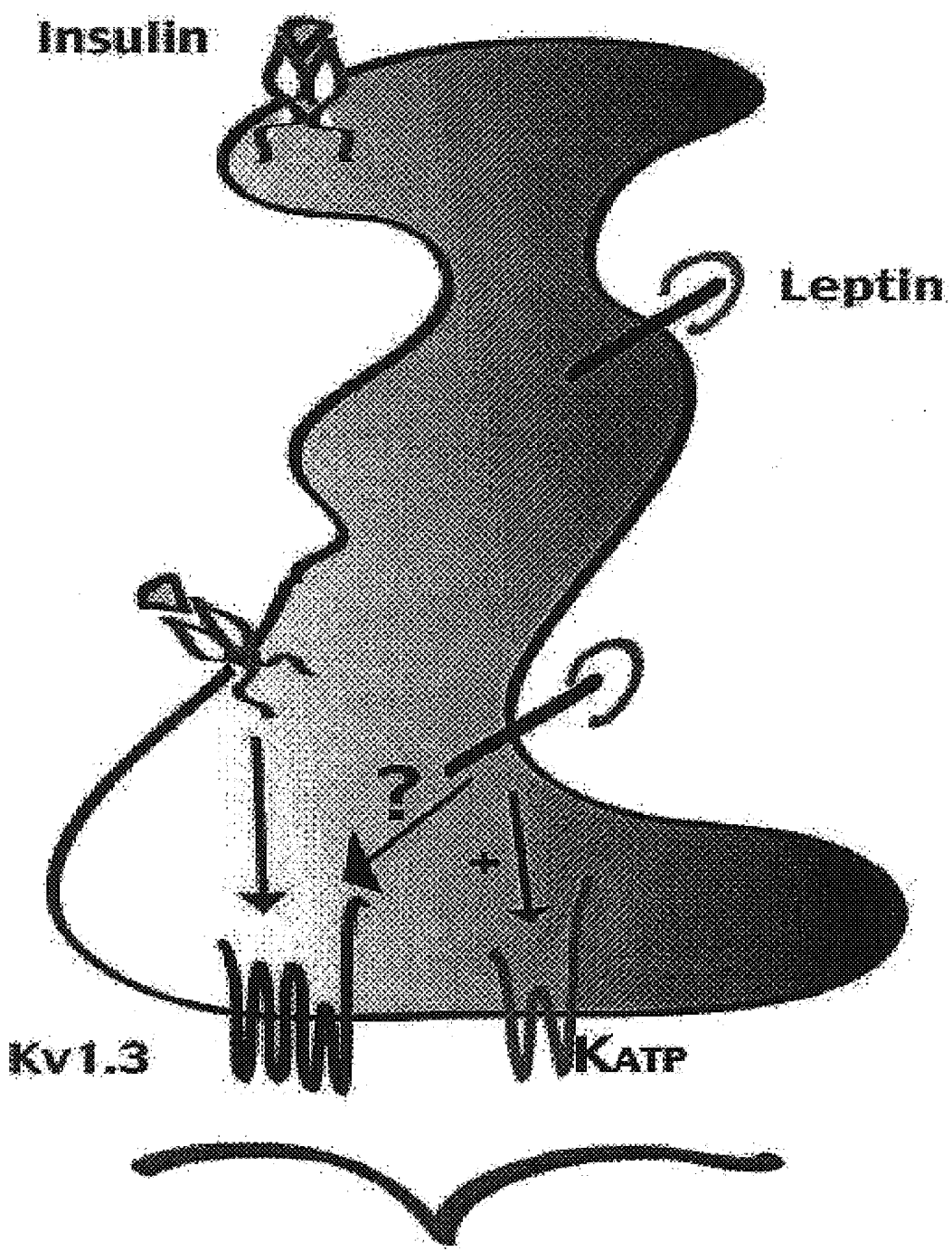
FIG. 1 is a diagram depicting a hypothalmic neuron detailing, without wishing to be bound by any particular theory, the proposed role of Kv1.3 in the regulation of body weight.
Figure 2:
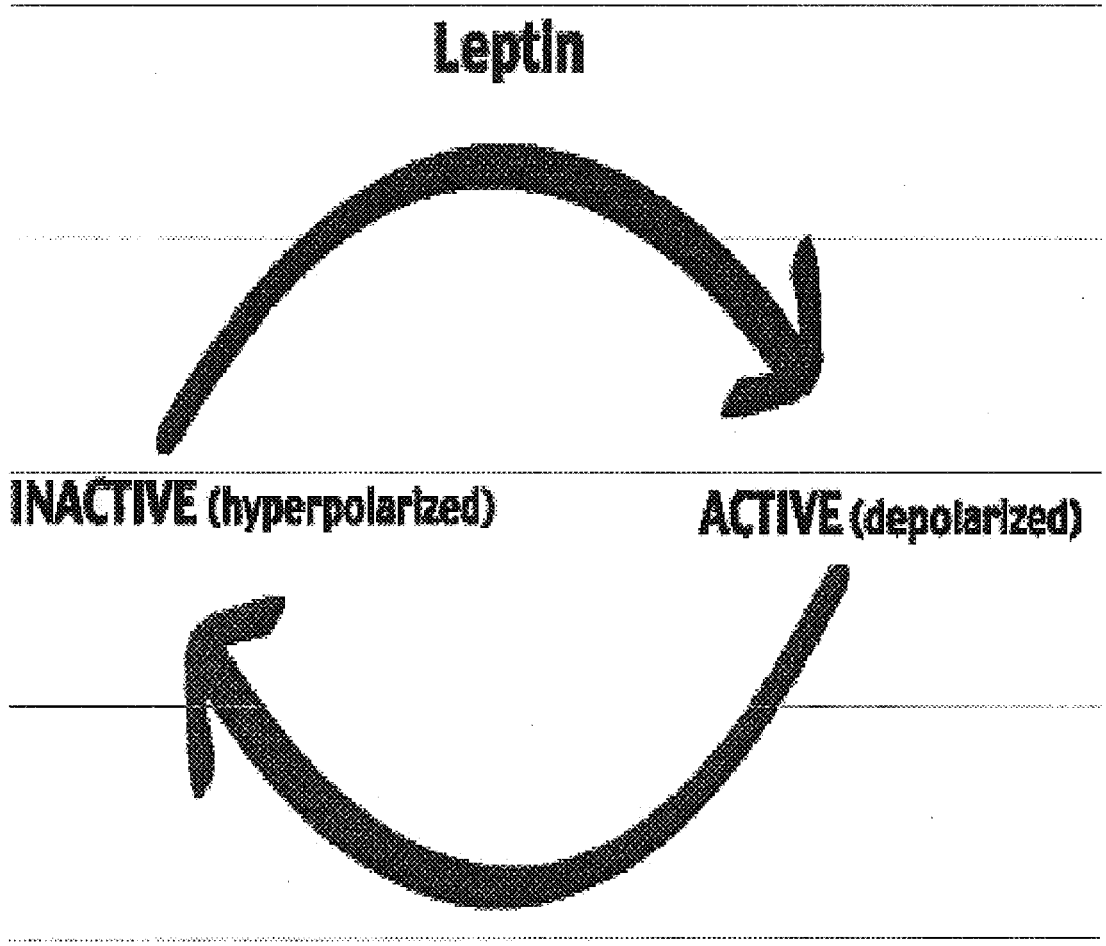
FIG. 2 is a diagram depicting, without wishing to be bound by any particular theory, the proposed role of leptin and Kv1.3 in the regulation of body weight.

The present invention is based on the surprising discovery that inhibition of a voltage-gated potassium channel, Kv1.3, decreases food intake, blood glucose level, body fat, and increases glucose uptake, insulin sensitivity, physical activity and metabolic rate. These unexpected results demonstrate that inhibition of Kv1.3 is a potential treatment for a disease, disorder or condition mediated by glucose metabolism, food intake, insulin insensitivity, and the like. Such a disease, disorder or condition includes, but is not limited to, obesity, diabetes, glucose intolerance, insulin resistance, hyperinsulemia, Syndrome X, hypercholesterolemia, hyperlipoproteinemia, hypertriglycereidemia, artherosclerosis, diabetic renal disease and the like.

The present invention also includes methods of identifying a useful compound in that, as demonstrated by the data disclosed herein, identifying a compound that inhibits Kv1.3 thereby identifies a useful compound for affecting a disease, disorder or condition mediated by glucose uptake, insulin insensitivity, increased body fat, decreased physical activities, decreased metabolic activity, and the like.

Definitions

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

By the term "applicator," as the term is used herein, is meant any device including, but not limited to, a hypodermic syringe, a pipette, and the like, for administering the inhibitor of Kv1.3 of the invention to a mammal.

The term "inhibitor" is used herein to refer to a composition of matter which when administered to a mammal such as a human, inhibits a biological activity attributable to the level or presence of an endogenous compound in the mammal.

The term "weight loss" is used herein to refer to a detectable decrease of body mass in an animal compared to the mass of the animal at a previous time.

The term "commercially relevant animal" is used herein to refer to a mammal that is raised and propagated for economically useful purposes, such as beef cattle, fowl, hogs, and farm raised fish, raised for comestible purposes and the like.

As used herein, "an effective amount of an Kv1.3 inhibitor" means an amount of a compound which effects a detectable decrease in the expression, activity, or both, of Kv1.3 in a cell, an animal, or both, compared with the level of expression, activity, or both, of Kv1.3 in an otherwise identical cell or animal to which the compound is not administered, or in the same cell or animal prior to administration of the compound.

The term "test compound" is used herein to refer to a composition of matter having at least one unknown effect when administered to an organism.

As used herein, the term "antisense nucleic acid molecule" means a nucleic acid polymer, at least a portion of which is complementary to a nucleic acid, which is present in a normal cell or in an affected cell. The antisense nucleic acid molecules of the invention preferably comprise between about ten and about one hundred nucleotides. Most preferably, the antisense nucleic acid molecules comprise between about fifteen and about fifty nucleotides. The antisense oligonucleotides of the invention include, but are not limited to, phosphorothioate oligonucleotides and other modifications of oligonucleotides. Methods for synthesizing oligonucleotides, phosphorothioate oligonucleotides, and otherwise modified oligonucleotides are well known in the art (U.S. Pat. No: 5,034,506; Nielsen et al., 1991, Science 254: 1497).

The term "increased insulin sensitivity" is used herein to refer to a state in which the effect of insulin is more pronounced than at other times or to a state where glucose uptake by peripheral tissues, such as muscle, liver, brain, fat, and kidney, is increased and glucose synthesis by peripheral tissues, such as liver, is decreased. Increased insulin sensitivity can be assessed using a variety of methods well known in the art, such as, but not limited to, methods for assessing a decrease in blood glucose level, insulin and glucose tolerance tests, insulin and glucose clamp, and assays that assess glucose uptake by a tissue or a cell.

"Instructional material," as that term is used herein, includes a publication, a recording, a diagram, or any other medium of expression which can be used to communicate the usefulness of the nucleic acid, peptide, and/or compound of the invention in the kit for effecting alleviating or treating the various diseases or disorders recited herein. Optionally, or alternately, the instructional material may describe one or more methods of alleviating the diseases or disorders in a cell or a tissue of a mammal. The instructional material of the kit may, for example, be affixed to a container that contains the nucleic acid, peptide, and/or compound of the invention or be shipped together with a container, which contains the nucleic acid, peptide, and/or compound. Alternatively, the instructional material may be shipped separately from the container with the intention that the recipient uses the instructional material and the compound cooperatively.

By the term "specifically binds," as used herein, is meant an antibody which recognizes and binds a Kv1.3 voltage-gated potassium channel, but does not substantially recognize or bind other molecules in a sample.

The term "glucose uptake" is used herein to refer to the process by which glucose enters a cell, whether in vivo or in vitro, which uptake need not, but can be associated with a concurrent decrease of glucose level external to the cell.

A "scorpion short toxin" is used herein to refer to a protein obtained from scorpion venom that is about 30–40 amino acids in length and comprises about 3–4 disulfide bridges, which protein inhibits a potassium channel. That is, the protein mediates a detectable decrease in potassium channel activity in the presence of the protein compared with potassium channel activity in the absence of the protein. A scorpion short toxin includes, but is not limited to, bmtx1, bmktx, bmtx2, bmp02, neurotoxin, tstx-k alpha, margatoxin, noxiustoxin, maurotoxin, charybdotoxin, scyllatoxin, agitoxin, chlorootoxin, butantoxin, toxin ts kappa, toxin I5a, toxin analog, toxin analog P01, OSK1 toxin, kaliotoxin, LQ2 toxin, pandinus toxin, and the like, as well as any scorpion short toxin discovered in the future.

"Potassium channel activity" is used herein to refer to the function of a protein that facilitates the translocation of potassium ions across a membrane. Potassium channel activity includes, inter alia, transport of a potassium ion across a membrane.

"Kv1.3 activity" is used herein to refer the function of the voltage-gated potassium channel Kv1.3, including, but not limited to, transport of potassium across a membrane, a change in membrane potential at the plasma or intracellular membrane compartment, subsequent change in cell metabolism such as, but not limited to, cell volume regulation, apoptosis, calcium flux, vesicle fusion, protein translocation, kinase and phosphatase regulation, and the like.

"Glucose metabolism" is used herein to refer to the use of the carbohydrate glucose in a physiological process.

A "glucose metabolism disease" or a "glucose metabolism disorder", as the terms are used synonymously herein, is an abnormal condition in which the carbohydrate glucose is not metabolized normally, e.g., the glucose is used and/or synthesized at a higher or lower level than it is compared with the level that is not associated with a disease or condition, leading to a disease state including obesity, diabetes, insulin resistance, glucose intolerance, hyperinsulemia, Syndrome X, hypercholesterolemia, hyperlipoproteinemia, hypertriglyceridemia, artherosclerosis, diabetic renal disease, and the like.

"Kv1.3 inhibiting" is used herein to refer to detectably decreasing the activity, function and/or expression of Kv1.3.

"Physical activity" is used herein to refer to any detectable movement, action, and/or alertness in an animal.

"Affecting physical activity" in an animal encompasses mediating a detectably higher or lower level of movement, action, and/or alertness in the animal, whereas decreasing physical activity in an animal is achieving a lower level of movement, action, and/or alertness.

"Metabolic rate" is used herein to refer to the use of calories or another energy source in an animal as assessed over a period of time. Hence, an increased metabolic rate is a higher level of the use of calories or another energy source by an animal over a period of time compared with the level of use of calories by an otherwise identical animal over the same period of time under substantially similar or identical conditions.

Description

I. Methods

A. Method of Treating and/or Preventing a Disease, Disorder or Condition

The present invention is based, in part, on the novel discovery that Kv1.3 plays a significant role in glucose metabolism in a mammal. As demonstrated by the data disclosed herein, inhibition of Kv1.3 can induce weight loss, decrease body fat, increase insulin sensitivity, affect appetite, decrease food intake, both treat and prevent obesity, and treat glucose metabolism diseases and disorders. Surprisingly, although prior studies suggested that Kv1.3 may be a potential IR substrate, the data disclosed here demonstrate that Kv1.3 is involved in the signal transduction pathway for food intake and weight control. Thereby, the present invention discloses methods to treat various diseases relating to food intake, glucose metabolism, and weight control, including, but not limited to, obesity, diabetes, insulin resistance, glucose intolerance, hyerinsulinemia, Syndrome X, hypercholesterolemia, hyperlipoproteinemia, hypertriglyceridemia, atherosclerosis, diabetic renal disease, and the like.

The present invention includes a method of inducing weight loss in an animal. This is because, as demonstrated by the data disclosed elsewhere herein, inhibition of Kv1.3, whether its expression, biological activity, or both, is inhibited, mediates a variety of physiological responses, including, but not limited to, increase cellular uptake of glucose, decreased body fat, decreased food intake, increased insulin sensitivity, increased physical activities, and increased metabolic rate. Thus, inhibiting Kv1.3 can be used to treat a wide variety of diseases, disorders or conditions where increasing glucose uptake, decreasing body fat, decreasing food intake, and/or increasing insulin sensitivity would provide a therapeutic benefit to an animal. Accordingly, one skilled in the art would appreciate, based upon the disclosure provided herein, that inhibiting Kv1.3 provides an important, novel therapeutic for treatment of, among other things, obesity, diabetes, insulin resistance, glucose intolerance, hyerinsulinemia, Syndrome X, hypercholesterolemia, hyperlipoproteinemia, hypertriglyceridemia, atherosclerosis, diabetic renal disease, and the like. More particularly, Kv1.3 can be inhibited thereby mediating weight loss in an animal; therefore, inhibition of Kv1.3 can be used to treat, among other things, obesity.

The skilled artisan would appreciate, based upon the disclosure provided herein, that an animal encompasses a bird, a fish, and a mammal, where the mammal includes, but is not limited to, a rodent, a cow, a pig, a sheep, a buffalo, a beefalo, a bison, a deer, a goat, and a human. One skilled in the art, armed with the teachings provided herein, would appreciate that the animal comprises a Kv1.3, which can be inhibited.

An inhibitor of Kv1.3 is administered to the animal thereby decreasing Kv1.3 and providing a therapeutic benefit. The skilled artisan would appreciate, based upon the disclosure provided herein, that Kv1.3 can be inhibited using a wide plethora of techniques well-known in the art or to be developed in the future. That is, the invention encompasses inhibiting Kv1.3 expression, e.g., inhibition of transcription and/or translation. This is because, as demonstrated by the data disclosed elsewhere herein, knocking-out the nucleic acid encoding Kv1.3, such that the nucleic acid was not transcribed or translated, mediated a variety of effects, including, but not limited to, increased insulin sensitivity, decreased food intake, loss of weight, and a decrease in body fat. Thus, inhibiting Kv1.3 includes, but is not limited to, inhibiting translation and/or transcription of a nucleic acid encoding the protein.

Further, the routineer would understand, based upon the disclosure provided elsewhere herein, that inhibition of Kv1.3 includes, but is not limited to, inhibiting the biological activity of the molecule. This is because, as the data disclosed elsewhere herein demonstrate, inhibition of Kv1.3 activity using a Kv1.3 inhibitor (e.g., margatoxin) mediated a decrease in food intake, body fat, and blood sugar level, as well as an increase in insulin sensitivity and glucose uptake by a cell. These data indicate that inhibition of Kv1.3 activity provides a therapeutic benefit for treatment of a disease, such as, but not limited to, obesity, diabetes, and the like.

The skilled artisan would understand that an inhibitor of Kv1.3 encompasses, but is not limited to, an inhibitor of a voltage-gated potassium channel, including, but not limited to, 4-aminopyridine, H-89 (N-[2-(p-bromocinnamylamino) ethyl]-5-isoquinolinesulfonamide), Hstx1, ShK-Dap$^{22}$, short scorpion toxin family (bmtx1, bmktx, bmtx2, bmp02, neurotoxin, tstx-k alpha, margatoxin, noxiustoxin, maurotoxin, charybdotoxin, scyllatoxin, agitoxin, chlorootoxin, butantoxin, toxin ts kappa, toxin I5a, toxin analog, toxin analog P01, OSK1 toxin, kaliotoxin, LQ2 toxin, pandinus toxin), clotrimazole, paxilline, stichodactyla toxin, melatonin, tetraethylammonium chloride, α-dendrotoxin, β-dendrotoxin, tityustoxin-Kα, noxiustoxin, agitoxin-2, κ-conotoxin, hanatoxin, hongotoxin, correolide, WIN 17317-3 (1-Benzyl-7-chloro-4-n-propylimino-1,4-dihydroquiniline), UK78282 (4-[(Diphenylmethoxy)methyl]-1-[3-(4-methyoxyphenyl)propyl]-piperidine), CP 339818 hydrochloride (N-[1-(Phenylmethyl)-4(1H)-quinolinylidene]-1 pentanamine hydrochloride), iberiotoxin, calcium channel blockers such as verapamil and nifedipine, fluxetime, serotonin uptake inhibitors, and serotonin agonists.

One skilled in the art, based upon the disclosure provided herein, would appreciate that Kv1.3 inhibition can be mediated by using, among other things, an antibody, an antisense nucleic acid, a ribozyme, a small molecule, a peptidomimetic, and a chemical compound, either known or to be developed, which inhibits Kv1.3 expression, activity, or both. That is, the invention encompasses using a Kv1.3 inhibiting compound such as, but not limited to, ShK-$^{Dap22}$, margatoxin, or kaliotoxin. This is because, as is demonstrated by the data disclosed elsewhere herein, inhibition of Kv1.3 expression and/or activity leads to reduced food intake, increased insulin sensitivity, reduced body weight, increased glucose sensitivity, and the like.

Further, one of skill in the art would, when equipped with this disclosure and the methods described herein, recognize that Kv1.3 inhibitors include such inhibitors as discovered in the future, as could be established by well known criteria in the art of pharmacology, and those identified in light of the physiological results of inhibition of Kv1.3 as described in detail herein. Therefore, the present invention is not limited in any way to the Kv1.3 inhibitors described herein, but includes those Kv1.3 inhibitors, and other voltage-gated potassium channel inhibitors, that inhibit, inter alia, Kv1.3, as are discovered in the future.

Methods of obtaining and generating voltage-gated potassium channel inhibitors are well known to those of ordinary skill in the art. For instance, a voltage-gated potassium channel inhibitors can be isolated from a naturally occurring source (e.g., scorpion venom, snake venom, soil fungus and sea anemone toxin). Moreover, a voltage-gated potassium channel inhibitor can be readily synthesized chemically. In addition, a voltage-gated potassium channel inhibitor can be obtained from a recombinant organism. For instance, compositions and methods for producing margatoxin from natural sources or from recombinant cells are well known in the art (Garcia et al., U.S. Pat. No. 5,494,895). Also, additional voltage-gated potassium channel inhibitors are well known to those of ordinary skill in the art, and are available from a variety of commercial sources (Calbiochem, San Diego, Calif.; Sigma Chemical Company, St. Louis, Mo.; Bachem Biosciences, King of Prussia, Pa.).

In another embodiment of the present invention, an inhibitor of Kv1.3 may be an antibody that specifically binds to Kv1.3 thereby inhibiting the action of Kv1.3 . Antibodies that specifically bind to Kv1.3 are well known to those of ordinary skill in the art (Veh et al., 1995, Eur. J. Neurosci. 7:2189–2205), can be purchased commercially (Voight Global Distribution LLC, Kansas City, Mo.), or can be produced using standard methods (Harlow et al., 1988, Antibodies: A Laboratory Manual, Cold Spring Harbor, N.Y.).

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879–5883; Bird et al., 1988, Science 242:423–426).

One of skill in the art will appreciate that an antibody can be administered as a protein, a nucleic acid construct encoding a protein, or both. Numerous vectors and other compositions and methods are well known for administering a protein or a nucleic acid construct encoding a protein to cells or tissues. Therefore, the invention includes a method of administering an antibody or nucleic acid encoding an antibody (synthetic antibody) that is specific for Kv1.3 (Sambrook et al., 1989, Molecular Cloning: A Laboratory Manual, Cold Spring Harbor Laboratory, New York; Ausubel et al., 1997, Current Protocols in Molecular Biology, John Wiley & Sons, New York).

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

One skilled in the art would understand, based upon the disclosure provided herein, that an antibody can be administered such that it inhibits the function of Kv1.3 present in a membrane. Moreover, the invention encompasses administering an antibody that specifically binds with Kv1.3, or a nucleic acid encoding the antibody, wherein the molecule further comprises an intracellular retention sequence such that antibody binds with the Kv1.3 and prevents its expression in a membrane. Such antibodies, frequently referred to as "intrabodies", are well known in the art and are described in, for example, Marasco et al. (U.S. Pat. No. 6,004,490) and Beerli et al. (1996, Breast Cancer Research and Treatment 38:11–17). Thus, the invention encompasses methods comprising inhibiting Kv1.3 where the Kv1.3 is present in a cell membrane, as well as methods of inhibiting Kv1.3 comprising inhibiting the Kv1.3 being present in the cell membrane, and such methods as become known in the future.

As noted previously elsewhere herein, the present encompasses inhibiting Kv1.3 by inhibiting expression of a nucleic acid encoding Kv1.3. Methods for inhibiting the expression of a gene are well known to those of ordinary skill in the art, and include the use of ribozymes or antisense nucleic acid molecules.

Antisense nucleic acid molecules are DNA or RNA molecules that are complementary to some portion of an mRNA molecule. When present in a cell, antisense nucleic acids hybridize to an existing mRNA molecule and inhibit translation into a gene product. Inhibiting the expression of a gene using an antisense nucleic acid molecule is well known in the art (Marcus-Sekura, 1988, Anal. Biochem. 172:289), as are methods to express an antisense nucleic acid molecule in a cell (Inoue, 1993, U.S. Pat. No. 5,190,931).

In one embodiment of the present invention, antisense nucleic acid molecules are synthesized and provided to the cell by way of methods well known to those of ordinary skill in the art. In one embodiment, antisense nucleic acid molecules are synthesized to be between about 10 and about 100, more preferably between about 15 and about 50 nucleotides long. The synthesis of nucleic acid molecules is well known in the art. In one embodiment of the present invention, the antisense nucleic acid molecule is modified to improve biological activity in comparison to unmodified antisense nucleic acid molecules (Tullis, 1991, U.S. Pat. No. 5,023,243).

The invention encompasses inhibition of expression of Kv1.3 using a ribozyme. Using ribozymes for inhibiting gene expression is well known to those of ordinary skill in the art (Cech et al., 1992, J. Biol. Chem. 267:17479; Hampel et al., 1989, Biochemistry 28: 4929; Altman et al., 1992, U.S. Pat. No. 5,168,053). Ribozymes are catalytic RNA molecules with the ability to cleave other single-stranded RNA molecules. Ribozymes are known to be sequence specific, and can therefore be modified to recognize a specific nucleotide sequence (Cech, 1988, J. Amer. Med. Assn. 260:3030), allowing the selective cleavage of specific mRNA molecules. Given the nucleotide sequence of Kv1.3 is well known in the art, one of ordinary skill in the art can synthesize an antisense polynucleotide or ribozyme without undue experimentation, provided with the disclosure and references incorporated herein.

The inhibitors of Kv1.3 or of Kv1.3 gene expression may be administered singly or in any combination thereof. Further, inhibitors of Kv1.3 may be administered singly or in any combination thereof in a temporal sense, in that they may be administered simultaneously, before, and/or after each other. One of ordinary skill in the art will appreciate the use of Kv1.3 inhibitors or inhibitors of Kv1.3 gene expression to affect weight loss, a treatment of obesity, and a method to increase insulin sensitivity, and will use the inhibitors detailed herein alone or in any combination to effect such results.

Thus, the invention encompasses a method for inducing weight loss where an inhibitor of Kv1.3 expression, activity, or both, is administered to an animal, thereby effecting a decreased food intake and thereby mediating weight in loss by the animal.

Similarly, the present invention encompasses a method for decreasing body fat in an animal. The method comprises administering a Kv1.3 inhibiting amount of a Kv1.3 inhibitor to the animal. This is because, as more fully set forth previously elsewhere herein, the data disclosed herein demonstrate that inhibition of Kv1.3 (expression, activity, or both) mediates a decrease in body fat, thereby decreasing body fat in the animal. More particularly, the data demonstrate that inhibition of Kv1.3 using, e.g., margatoxin, mediated a decrease in body fat in an animal. Thus, the present invention includes a method of decreasing body fat in an animal by inhibiting Kv1.3 where the data disclosed demonstrate that inhibiting Kv1.3 also decreases body fat, among other things.

One skilled in the art would appreciate that having a leaner animal, i.e., an animal with decreased body fat, would provide a benefit in that such an animal would be useful in providing a leaner source of meat having a decreased amount of fat. Such animal includes, but is not limited to, a bird, a fish, a rodent, a cow, a pig, a sheep, a buffalo, a beefalo, a bison, a deer, and a goat. Basically, the invention includes producing an animal comprising a decreased body fat content where the animal is used for human consumption.

One skilled in the art would also understand, based upon the disclosure provided herein, that the invention encompasses a method for increasing insulin sensitivity in a mammal. The method comprises administering a Kv1.3 inhibitor to a mammal. This is because, as stated previously elsewhere herein, inhibiting Kv1.3, which is a voltage-gated potassium channel, increases insulin sensitivity in the mammal. Also, as discussed previously, inhibition of Kv1.3 includes inhibiting expression of a nucleic acid encoding Kv1.3, as well as, but not limited to, inhibiting the biological activity of the protein using, among other things, an antibody, a ribozyme, an antisense, a peptidomimetic, and the like. Again, this is because it has been demonstrated elsewhere herein that inhibiting Kv1.3 expression and/or function, mediated an increase in insulin sensitivity.

The invention includes a method for decreasing food intake in a mammal. Basically, the method comprises administering a Kv1.3 inhibiting amount of a Kv1.3 inhibitor to a mammal. This, in turn, decreases food intake in the mammal. This is because, as disclosed elsewhere herein, the data demonstrate that inhibition of Kv1.3 mediates a decrease in the food intake by a mammal compared to an otherwise identical animal to which the inhibitor is not administered or compared with the food intake by the same animal before administration of the Kv1.3 inhibitor. Thus, the invention encompasses a method of decreasing food intake by inhibiting Kv1.3.

The amount, dosing regimen, and route of administration for inhibiting Kv1.3 in an animal can be readily determined by one skilled in the art and would depend on well-known factors, including, but not limited to, the age and condition of the animal, the weight and body fat content of the animal, and the desired weight and/or body fat content of the animal. The dosage and route of administration can be easily determined as exemplified elsewhere herein using art-recognized models of obesity and diabetes, and therefore, the skilled artisan would understand, based upon the disclosure provided herein, precisely how to inhibit Kv1.3 to practice the methods of the invention.

Similarly, the invention includes a method for affecting appetite in a mammal. Once again, the method comprises administering a Kv1.3 inhibiting amount of a Kv1.3 inhibitor to a mammal, thereby affecting appetite in the mammal. This is because, as discussed previously elsewhere herein, the data disclosed demonstrate that inhibition of Kv1.3 decreases appetite, as indicated by decreased food intake, in a mammal. This method is useful for providing a therapeutic benefit where the mammal is in need of reducing their appetite, such as when, for instance, the mammal is obese and/or suffers from diabetes or any other disease mediated by, or associated with, increased weight.

The invention encompasses a method for treating obesity in a mammal. The method comprises administering a Kv1.3 inhibiting amount of a Kv1.3 inhibitor to a mammal. As demonstrated by the data disclosed herein, including, but not limited to, data demonstrating weight loss by obese mice using an art-recognized model of obesity, by inhibiting Kv1.3 in the mice, inhibiting Kv1.3 inhibits food intake, decreases weight, and increases insulin sensitivity, thereby treating obesity in the mammal.

The present invention includes a method for preventing obesity in a mammal. The method comprises administering a Kv1.3 inhibiting amount of a Kv1.3 inhibitor to a mammal. This is because the data disclosed elsewhere herein demonstrate that inhibiting Kv1.3 not only treats obesity, but also actually prevents obesity in an art-recognized model of obesity. Thus, the skilled artisan would appreciate, based on the teachings provided herein, that the invention includes, but is not limited to, a method for preventing obesity in a mammal.

The invention encompasses a method for treating a glucose-metabolism disease or disorder in a mammal. The method comprises administering a Kv1.3 inhibiting amount of a Kv1.3 inhibitor to a mammal. This is because, as discussed previously elsewhere herein, the data disclosed herein demonstrate that inhibiting Kv1.3 mediates a variety of effects, including, inter alia, increased glucose uptake, decreased insulin resistance, and reduction of food intake. Thus, the routineer would appreciate, based upon the disclosure provided herein, that inhibiting Kv1.3 can treat a glucose-metabolism disease or disorder.

The present invention further includes a method for affecting physical activity in an animal. The method comprises administering a Kv1.3 inhibiting amount of a Kv1.3 inhibitor to an animal thereby affecting physical activity. This is because, as demonstrated by the data disclosed elsewhere herein, of Kv1.3 affects a number of physiological responses, including, but not limited to increased physical activities. Thus, inhibiting Kv1.3 can be used to treat a wide variety of disorders, diseases, and/or conditions where increasing glucose uptake, decreasing body fat, affecting activity, decreasing food intake, and/or increasing insulin sensitivity would provide a therapeutic benefit to mammal. Therefore, the skilled artisan will appreciate, based on the disclosure provided herein, that surprisingly, inhibition of Kv1.3 provides a novel method for affecting the physical activity of an animal.

One skilled in the art would understand, based upon the disclosure provided herein, that affecting Kv1.3 encompasses both inhibiting and increasing Kv1.3 expression, activity, or both. This is because the skilled artisan would appreciate, once armed with the teachings provided herein, that inhibiting Kv1.3 increases physical activity such that increasing Kv1.3 activity and/or expression can decrease physical activity in an animal. Thus, the present invention includes increasing and decreasing Kv1.3 activity and/or expression thereby either increasing or decreasing physical activity in an animal. Preferably, Kv1.3 activity and/or expression is inhibited thereby increasing physical activity in an animal.

The skilled artisan would further appreciate, once armed with the teachings provided herein, that a method of increasing physical activity can be used to treat a disease or condition mediated by, or associated with, decreased physical activity. Such diseases or conditions include, but are not limited to, depression, narcolepsy, fatigue, and the like.

The present invention includes a method of affecting metabolic rate in an animal. This is because, as demonstrated by the data disclosed elsewhere herein, inhibition of Kv1.3 affects a variety of physiological processes, including, but not limited to, decreased food intake, increased physical activities, and increased metabolic rate. Thus, the data disclosed herein demonstrate that inhibiting Kv1.3 can affect metabolic rate in an animal. Accordingly, one skilled in the art would appreciate, based upon the disclosure provided herein, that inhibiting Kv1.3 provides an important, novel therapeutic for treatment of, among other things, obesity, diabetes, insulin resistance, glucose intolerance, hyerinsulinemia, Syndrome X, hypercholesterolemia, hyperlipoproteinemia, hypertriglyceridemia, atherosclerosis, diabetic renal disease, and the like, where affecting the metabolic rate mediates a therapeutic benefit. More particularly, Kv1.3 can be inhibited thereby affecting metabolic rate in an animal; therefore, inhibition of Kv1.3 can be used to treat, among other things, obesity and other diseases, disorders and conditions related to decreased metabolic rate.

However, the present invention is not limited to increasing the metabolic rate. Rather, the invention encompasses methods for decreasing the metabolic rate where such decrease would provide a benefit. This is because the data disclosed herein demonstrate that inhibiting Kv1.3 mediates an increase in metabolic rate such that increasing Kv1.3 can decrease metabolic rate. Decreasing the metabolic rate in an animal can be used, for instance, where weight gain and/or increased body fat content in the animal is desired or would provide a therapeutic benefit. Conditions and diseases where decreased metabolic rate, increased body fat, decreased glucose uptake, and the like, is desirable would be readily apparent to one skilled in the art based upon the disclosure provided herein.

The skilled artisan would appreciate, based upon the teachings provided herein, that a glucose-metabolism disease or disorder is selected from the group consisting of type II diabetes mellitus, obesity, insulin resistance, hyerinsulinemia, Syndrome X, hypercholesterolemia, hyperlipoproteinemia, hypertriglyceridemia, artherosclerosis, glucose intolerance, diabetic nephropathy and the like.

The invention includes a method for increasing physical activity and/or metabolic rate in a mammal. The skilled artisan would appreciate, based upon the teachings provided herein, that Kv1.3 inhibitors can treat physical activity-related diseases or disorders such as narcolepsy, depression, and the like, and that the Kv1.3 inhibitors can be used to treat metabolism-related disease such as obesity.

The invention also encompasses the use of a pharmaceutical composition comprising an appropriate Kv1.3 inhibitor to practice the methods of the invention, where the composition comprises an appropriate Kv1.3 inhibitor, which can be used in an amount sufficient to inhibit Kv1.3 thereby producing a therapeutic effect, and a pharmaceutically acceptable carrier.

The pharmaceutical compositions useful for practicing the invention may be administered to deliver a dose of between 1 ng/kg/day and 100 mg/kg/day.

Pharmaceutical compositions that are useful in the methods of the invention may be administered systemically in oral solid formulations, ophthalmic, suppository, aerosol, and topical or other similar formulations. In addition to the appropriate Kv1.3 inhibitor, such pharmaceutical compositions may contain pharmaceutically acceptable carriers and other ingredients known to enhance and facilitate drug administration. Other possible formulations, such as nanoparticles, liposomes, resealed erythrocytes, and immunologically based systems may also be used to administer an appropriate Kv1.3 inhibitor according to the methods of the invention.

Compounds, which are identified using any of the methods described herein, may be formulated and administered to a mammal for treatment of the diseases disclosed herein are now described.

The invention encompasses the preparation and use of pharmaceutical compositions comprising a compound useful for treatment of the diseases disclosed herein as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions, are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats and dogs, and birds including commercially relevant birds such as chickens, ducks, geese, and turkeys.

Pharmaceutical compositions that are useful in the methods of the invention may be prepared, packaged, or sold in formulations suitable for oral, rectal, vaginal, parenteral, topical, pulmonary, intranasal, buccal, ophthalmic, intrathecal or another route of administration. Other contemplated formulations include projected nanoparticles, liposomal preparations, resealed erythrocytes containing the active ingredient, and immunologically based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e. about 20° C.) and which is liquid at the rectal temperature of the subject (i.e. about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants and preservatives.

A pharmaceutical composition of the invention may be prepared, packaged, or sold in a formulation suitable for vaginal administration. Such a composition may be in the form of, for example, a suppository, an impregnated or coated vaginally-insertable material such as a tampon, a douche preparation, or gel or cream or a solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e. such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid carrier. As is well known in the art, douche preparations may be administered using, and may be packaged within, a delivery device adapted to the vaginal anatomy of the subject. Douche preparations may further comprise various additional ingredients including, but not limited to, antioxidants, antibiotics, antifungal agents, and preservatives.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1–1.0% (w/w) solution or suspension of the active ingredient in an aqueous or oily liquid carrier. Such drops may further comprise buffering agents, salts, or one or more other of the additional ingredients described herein. Other opthalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, *Remington's Pharmaceutical Sciences*, Mack Publishing Co., Easton, Pa., which is incorporated herein by reference.

Typically dosages of the compound of the invention which may be administered to an animal, preferably a human, range in amount from 1 µg to about 100 g per kilogram of body weight of the animal. While the precise dosage administered will vary depending upon any number of factors, including but not limited to, the type of animal and type of disease state being treated, the age of the animal and the route of administration. Preferably, the dosage of the compound will vary from about 1 mg to about 10 g per kilogram of body weight of the animal. More preferably, the dosage will vary from about 10 mg to about 1 g per kilogram of body weight of the animal.

The compound may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc.

B. A Method of Identifying a Useful Compound

The invention encompasses a method for identifying a compound that inhibits Kv1.3. One skilled in the art would appreciate, based upon the disclosure provided herein, that assessing the expression, activity, or both, of Kv1.3 can be performed by assessing, among other things, the levels of Kv1.3 in an animal, and the like, when compared to the same parameter in an otherwise identical animal not treated with the compound. One skilled in the art would understand that such compounds can be useful for increasing cellular glucose uptake, decreasing food intake, decreasing percent body fat, increasing insulin, increasing the resting metabolic activity, lowering blood glucose levels, and initiating weight loss. This is because the data disclosed elsewhere herein demonstrate, for the first time, that inhibiting Kv1.3 (expression, activity, or both) mediates a variety of beneficial effects, including, but not limited to, increased insulin sensitivity, decreased food intake, decreased body fat, weight loss, decreased caloric intake, increased resting metabolic activity, lowered blood glucose levels, and initiating weight loss. This is because the present invention discloses, for the first time, that Kv1.3 expression is associated with, or mediates, such diseases, conditions and disorders. Accordingly, the data disclosed elsewhere suggest that inhibiting of Kv1.3 can provides a useful therapeutic for those diseases, disorders or conditions.

Thus, the skilled artisan, once armed with the teachings of the invention, would appreciate that a compound that inhibits Kv1.3 is a powerful potential therapeutic treatment of a glucose metabolism mediated disease, such that identification of such a compound identifies a potential therapeutic for such disease The method comprises administering to a mammal a compound and comparing the level of Kv1.3 activity in the mammal before and after administration of the compound. The routineer would understand, based on the disclosure provided herein, that a lower level of Kv1.3 activity in the mammal after administration of the compound compared with the level of Kv1.3 activity before administration of the compound indicates that the compound is useful for treating a disorder, condition or disease mediated by glucose metabolism, including, but not limited to, diabetes, obesity, insulin resistance, hyerinsulinemia, Syndrome X, hypercholesterolemia, hyperlipoproteinemia, hypertriglyceridemia, artherosclerosis, glucose intolerance, diabetic nephropathy and the like.

This is because, as stated previously elsewhere herein, it has been discovered that inhibiting Kv1.3 activity in an animal treats a disease associated with Kv1.3 expression and/or activity. The skilled artisan would also appreciate, in view of the disclosure provided herein, that assays to determine the level of Kv1.3 activity and/or expression in a mammal include those well known in the art, or those to be developed in the future, all of which can be used to assess the level of Kv1.3 activity in a mammal before and after administration of the compound. The skilled artisan would further appreciate that Kv1.3 activity, as disclosed elsewhere herein, includes an association with resting metabolism rate, caloric consumption, insulin sensitivity, glucose uptake, and the like. Further, the invention encompasses a compound identified using this method.

The invention further includes another method for identifying a compound useful for treating a disease mediated by a glucose-mediated disease in a mammal. More specifically, the method comprises identifying a compound that inhibits Kv1.3 by assessing the level of Kv1.3 activity in mammal administered the compound in comparison with an identical mammal to which the compound is not administered. A lower level of Kv1.3 activity in the mammal administered the compound when compared to an identical mammal not administered the compound is an indication that the compound is useful for inhibiting Kv1.3 activity. And, since the present invention discloses, for the first time, that Kv1.3 plays a role in glucose mediated or associated disorders including diabetes, syndrome X, obesity and the like, in that inhibiting Kv1.3 effects a variety of responses relating to such diseases or disorders, identifying a compound that inhibits Kv1.3 therefore identifies a compound useful for treating a disease mediated by abnormal glucose metabolism. Such diseases include, but are not limited to, diabetes, obesity, insulin resistance, hyerinsulinemia, Syndrome X, hypercholesterolemia, hyperlipoproteinemia, hypertriglyceridemia, artherosclerosis, glucose intolerance, diabetic nephropathy and the like. Clearly, as demonstrated elsewhere herein, a compound that inhibits Kv1.3 is an important potential therapeutic compound useful for treatment of diseases associated with glucose metabolism given the role that Kv1.3 plays in glucose metabolism and regulation of food intake and body weight and fat content, all of which are demonstrated elsewhere herein for the first time.

The invention further includes another method of identifying a compound that useful for treating obesity. The method comprises assessing the level of Kv1.3 activity in a mammal after administration of a compound compared to a standard baseline previously established for that particular species of mammal before administration of the compound. Methods of assaying Kv1.3 activity are disclosed elsewhere herein, but can include assessing caloric intake, resting metabolic activity, blood glucose levels, insulin sensitivity, glucose uptake by cells, amount of food intake, and weight loss. A decrease in Kv1.3 activity in a mammal after administration of a compound compared to the baseline level of Kv1.3 activity determined for the that particular species of mammal before administration of a compound can indicate that a compound is useful in inhibiting the activity of Kv1.3, and is therefore useful in the treatment of obesity. This is because, as discussed previously elsewhere herein, inhibition of Kv1.3 mediates a decrease in, among other things, food intake and weight, thereby treating obesity, such that it would be appreciated by the skilled artisan, based on the disclosure provided herein, that a compound that inhibits Kv1.3 can be used to treat obesity.

The invention encompasses a method of identifying a compound that is useful for treating obesity. The method comprises assessing the level of Kv1.3 activity in a mammal after administration of a compound compared to the level of Kv1.3 in the same mammal prior to the administration of the compound, or to the level of Kv1.3 activity in an otherwise identical mammal to which the compound is not administered. A decrease in Kv1.3 activity in a mammal after administration of a compound compared to the level of Kv1.3 activity determined for the mammal prior to the administration of the compound, or compared with the level of Kv1.3 activity in the otherwise identical mammal to which the compound is not administered, is an indication that the compound is useful for the treatment of obesity. This is because, as more fully discussed elsewhere herein, the data disclosed herein demonstrate, for the first time, that inhibiting the activity of Kv1.3 mediates a decrease in, among other things, food intake and weight, thereby treating obesity, such that it would be appreciated by the skilled artisan, based on the disclosure provided herein, that a compound that inhibits Kv1.3 can be used to treat obesity.

The invention encompasses a method of identifying a compound that is useful for treating obesity. The method comprises assessing the level of Kv1.3 activity in a cell after the cell is contacted with a compound compared with the level of Kv1.3 in an otherwise identical cell which is not contacted with the compound. A decrease in Kv1.3 activity in the cell contacted with the compound compared with the level of Kv1.3 activity in the otherwise identical cell not contacted with the compound is an indication that the compound is useful for the treatment of obesity. This is because, as more fully discussed elsewhere herein, the data disclosed herein demonstrate, for the first time, that inhibiting the activity of Kv1.3 mediates a decrease in, among other things, food intake and weight, thereby treating obesity, such that it would be appreciated by the skilled artisan, based on the disclosure provided herein, that a compound that inhibits Kv1.3 can be used to treat obesity.

The skilled artisan would appreciate, based upon the disclosure provided herein, that the cell used to assess the level of Kv1.3 activity due to the cell being contacted with a compound can be selected from the group consisting of a skeletal muscle cell, a fat cell, a liver cell, a brain cell, a kidney cell, and a pancreas cell. Further, the skilled artisan would understand, based upon the teachings provided herein, that a skeletal muscle cell includes, but is not limited to, a rat L6 cell, a mouse NOR-10 cell, a mouse BLO-11 cell, a mouse BC3H1 cell, a rat H9c2 cell, a mouse G-7 cell, a rat L8 cell, a mouse c2C12 cell, a mouse P19 cell, and the like.

The skilled artisan would appreciate, based upon the disclosure provided herein, that for each of the methods of identifying a compound of interest, the invention encompasses any compound identified thereby.

II. Kits

The invention encompasses various kits relating to inhibiting Kv1.3 in an animal because, as disclosed elsewhere herein, inhibiting Kv1.3 effects, inter alia, increased glucose uptake, decreased food intake, increased metabolic activity, weight loss, decreased fat content, and the like, such that inhibiting Kv1.3 provides, among other things, a novel method of treating glucose metabolism mediated disorders in an animal. Thus, in one aspect, the invention includes a kit for treating a glucose-mediated disorder in an animal. The kit comprises an effective amount of a Kv1.3 inhibitor. The kit further comprises an applicator and an instructional material for the use thereof.

The invention includes various kits which comprise a compound, such as, but not limited to, an antibody that specifically binds Kv1.3 as well as a nucleic acid encoding such an antibody, a nucleic acid complementary to a nucleic acid encoding a Kv1.3 but in an antisense orientation with respect to transcription, a ribozyme capable of cleaving single-stranded Kv1.3 RNA, an applicator, and instructional materials which describe use of the compound to perform the methods of the invention. Although exemplary kits are described below, the contents of other useful kits will be apparent to the skilled artisan in light of the present disclosure. Each of these kits is included within the invention.

The invention encompasses a kit for treating obesity in an animal. The kit comprises an effective amount of a Kv1.3 inhibitor, an applicator, and an instructional material for the use of the kit. As more fully set forth elsewhere herein, the inhibitor includes, but is not limited to, an antibody, an antisense molecule, a ribozyme, a peptidomimetic, a chemical compound, and the like, that inhibits Kv1.3 expression, activity, or both. The kit encompasses a kit comprising at least two Kv1.3 inhibitors. The skilled artisan would appreciate, based upon the disclosure provided elsewhere herein, that a kit comprising a Kv1.3 inhibitor can be used to treat obesity since the data disclosed herein demonstrate that inhibition of Kv1.3 increases glucose uptake, increases insulin sensitivity, decreases body fat, decreases food intake, and decreases weight. One skilled in the art would understand, once armed with the teachings provided herein, that these effects of Kv1.3 inhibition can treat obesity.

The invention also includes a kit for inducing weight loss in an animal. The kit comprises an effective amount of a Kv1.3 inhibitor, an applicator, and an instructional material for the use of the kit. As more fully set forth elsewhere herein, the inhibitor includes, but is not limited to, an antibody, an antisense molecule, a ribozyme, a peptidomimetic, a chemical compound, and the like, that inhibits Kv1.3 expression, activity, or both. This is because, as the skilled artisan would appreciate, based on the disclosure provided elsewhere herein, that a kit comprising a Kv1.3 inhibitor can be used to induce weight loss in an animal since the data disclosed elsewhere herein demonstrate that inhibition of Kv1.3 increases glucose uptake, increases insulin sensitivity, decreases body fat, decreases food intake, and decreases weight. One skilled in the art would understand, once armed with the teachings provided herein, that these effects of Kv1.3 inhibition can thereby induce weight loss.

The invention further encompasses a kit for decreasing body fat in an animal. The kit comprises an effective amount of a Kv1.3 inhibitor, an applicator, and an instructional material for the use of the kit. This is because, as the skilled artisan would appreciate, based on the disclosure provided elsewhere herein, that a kit comprising a Kv1.3 inhibitor can be used to decrease body fat in an animal since the data disclosed elsewhere herein demonstrate that inhibition of Kv1.3 increases the metabolic rate, increases insulin sensitivity, decreases weight, decreases food intake, and decreases body fat. As set forth elsewhere herein, the inhibitor includes, but is not limited to, an antibody, an antisense molecule, a ribozyme, a peptidomimetic, a chemical compound, and the like, that inhibits Kv1.3 expression, activity, or both. One skilled in the art would understand, once armed with the teachings provided herein, that these effects of Kv1.3 inhibition can thereby decrease body fat in an animal.

The invention also includes a kit for increasing insulin sensitivity in an animal. The skilled artisan will appreciate, when equipped with the present disclosure, that the data disclosed elsewhere herein demonstrate that inhibition of Kv1.3, inter alia increases the metabolic rate, increases glucose uptake, and increases insulin sensitivity. Thus, a kit comprising an effective amount of a Kv1.3 inhibitor, an applicator, and an instructional material can be used to increase insulin sensitivity in an animal. As set forth elsewhere herein, the inhibitor includes, but is not limited to, an antibody, an antisense molecule, a ribozyme, a peptidomimetic, a chemical compound, and the like, that inhibits Kv1.3 expression, activity, or both. Therefore, one skilled in the art would understand, once armed with this disclosure and the data disclosed herein, that the effects of Kv1.3 inhibition can increase insulin sensitivity in an animal.

The invention encompasses a kit for decreasing food intake in an animal. The kit comprises an effective amount of a Kv1.3 inhibitor, an applicator, and an instructional material for the use of the kit. As more fully set forth elsewhere herein, the inhibitor includes, but is not limited to, an antibody, an antisense molecule, a ribozyme, a peptidomimetic, a chemical compound, and the like, that inhibits Kv1.3 expression, activity, or both. The kit encompasses where the kit comprises at least two Kv1.3 inhibitors. The skilled artisan would appreciate, based upon the disclosure provided elsewhere herein, that a kit comprising a Kv1.3 inhibitor can be used to decrease food intake in an animal since the data disclosed herein demonstrate that inhibition of Kv1.3 decreases weight, increases insulin sensitivity, decreases body fat, and decreases food intake. One skilled in the art would understand, once armed with the teachings provided herein, that these effects of Kv1.3 inhibition can decrease food intake in an animal.

The invention further encompasses a kit for affecting appetite in an animal. The kit comprises an effective amount of a Kv1.3 inhibitor, an applicator, and an instructional material for the use of the kit. This is because, as the skilled artisan would appreciate, based on the disclosure provided elsewhere herein, that a kit comprising a Kv1.3 inhibitor can be used to affect appetite in an animal since the data disclosed elsewhere herein demonstrate that inhibition of Kv1.3 increases the metabolic rate, increases insulin sensitivity, decreases weight, decreases food intake, and affects appetite. As set forth elsewhere herein, the inhibitor includes, but is not limited to, an antibody, an antisense molecule, a ribozyme, a peptidomimetic, a chemical compound, and the like, that inhibits Kv1.3 expression, activity, or both. One skilled in the art would understand, once armed with the teachings provided herein, that these effects of Kv1.3 inhibition can thereby affect appetite in an animal.

The invention also encompasses a kit for preventing obesity in an animal. Briefly, and as set forth more fully elsewhere herein, a kit comprising a Kv1.3 inhibitor, an applicator, and an instructional material for the use of the kit, can be used for preventing obesity in an animal. This is because, as one of skill in the art would appreciate when equipped with the present disclosure and the data disclosed herein, that a kit comprising a Kv1.3 inhibitor can be used to, inter a lia, increase insulin sensitivity, decrease weight, decrease food intake, treat obesity, and prevent obesity. As set forth elsewhere herein, the inhibitor includes, but is not limited to, an antibody, an antisense molecule, a ribozyme, a peptidomimetic, a chemical compound, and the like, that inhibits Kv1.3 expression, activity, or both. Therefore, one of skill in the art would understand that a kit comprising a Kv1.3 inhibitor can be used to prevent obesity in an animal.

The invention also includes a kit for treating a glucose metabolism disease in an animal. The skilled artisan will appreciate, when equipped with the present disclosure, that the data disclosed elsewhere herein demonstrate that inhibition of Kv1.3 increases the metabolic rate, increases glucose uptake, and treats a glucose metabolism disease. Thus, a kit comprising an effective amount of a Kv1.3 inhibitor, an applicator, and an instructional material can be used to treat a glucose metabolism disease in an animal. As set forth elsewhere herein, the inhibitor includes, but is not limited to, an antibody, an antisense molecule, a ribozyme, a peptidomimetic, a chemical compound, and the like, that inhibits Kv1.3 expression, activity, or both. As further set forth elsewhere herein, a glucose metabolism disease, includes, but is not limited to diabetes, obesity, insulin resistance, hyerinsulinemia, Syndrome X, hypercholesterolemia, hyperlipoproteinemia, hypertriglyceridemia, artherosclerosis, glucose intolerance, diabetic nephropathy and the like. Therefore, one skilled in the art would understand, once armed with this disclosure and the data disclosed herein, that a kit comprising a Kv1.3 inhibitor can treat a glucose metabolism disease in an animal.

The invention further encompasses a kit for affecting physical activity in an animal. The kit comprises an effective amount of a Kv1.3 inhibitor, an applicator, and an instructional material for the use of the kit. This is because, as the skilled artisan would appreciate, based on the disclosure provided elsewhere herein, that a kit comprising a Kv1.3 inhibitor can be used to affect physical activity in an animal since the data disclosed elsewhere herein demonstrate that inhibition of Kv1.3 increases the metabolic rate, increases insulin sensitivity, treats obesity, decreases food intake, and affects physical activity. As set forth elsewhere herein, the inhibitor includes, but is not limited to, an antibody, an antisense molecule, a ribozyme, a peptidomimetic, a chemical compound, and the like, that inhibits Kv1.3 expression, activity, or both. One skilled in the art would understand, once armed with the teachings provided herein, that these effects of Kv1.3 inhibition can thereby affect physical activity in an animal.

The invention also encompasses a kit for affecting metabolic rate in an animal. Briefly, and as set forth more fully elsewhere herein, a kit comprising a Kv1.3 inhibitor, an applicator, and an instructional material for the use of the kit, can be used for preventing obesity in an animal. This is because, as one of skill in the art would appreciate when equipped with the present disclosure and the data disclosed herein, that a kit comprising a Kv1.3 inhibitor can be used to, inter alia, increase insulin sensitivity, decrease weight, decrease food intake, affect physical activity and affect metabolic rate. As set forth elsewhere herein, the inhibitor includes, but is not limited to, an antibody, an antisense molecule, a ribozyme, a peptidomimetic, a chemical compound, and the like, that inhibits Kv1.3 expression, activity, or both. Therefore, one of skill in the art would understand that a kit comprising a Kv1.3 inhibitor can be used to affect metabolic rate in an animal.

III. Transgenic Animals

The skilled artisan will appreciate, as disclosed elsewhere herein, that a transgenic animal comprising a deficiency in Kv1.3 is useful in the study of glucose metabolism mediated disorders, diseases, and conditions, including, but not limited to, obesity, diabetes, and the like.

The skilled artisan will also appreciate, when armed with the present disclosure, that a transgenic animal comprising a deficiency in Kv1.3 is useful in that the transgenic mammal will comprise a lower amount of body fat, and is therefore a more healthful animal for human consumption. That is because, as disclosed herein, a transgenic animal comprising a deficiency in Kv1.3 is of a similar size to a counterpart animal comprising a functional Kv1.3, but the transgenic animal comprises less body fat, and is therefore a leaner animal. Further, it would be understood by the routineer, based upon the disclosure provided herein, that a reduction in consumption in animal fat is widely regarded as a method to not only reduce obesity, but to maintain and improve cardiovascular health and to prevent and/or treat diabetes.

The present invention encompasses a non-human transgenic animal which is commercially relevant as a food stuff for human consumption, as well as animals not used as food stuffs, but where a leaner animal is of some benefit either to the animal or to humans. Such animals include, but are not limited to, a bird, a rodent, a cow, a pig, a sheep, a buffalo, a beefalo (a cow/buffalo hybrid animal), a bison, a deer, a goat, and the like.

In addition, the skilled artisan would appreciate, based upon the disclosure provided herein, that a transgenic non-human mammal lacking Kv1.3 function is a useful model system for the study of a disease or condition associated with, or mediated by, Kv1.3 function, including a condition where lack of Kv1.3 provides a benefit to the mammal. Thus, the transgenic non-human mammal of the invention is not only useful as a leaner comestible, but also provides a useful model system for studying the role of Kv1.3 function, especially as it relates to obesity, diabetes, food intake, insulin sensitivity, and body weight control.

The present invention therefore includes a transgenic non-human animal comprising a deficiency in Kv1.3. The skilled artisan will appreciate, when equipped with this disclosure and the data contained herein, that an animal deficient in Kv1.3 comprises an animal that lacks the Kv1.3 gene in its entirety, or any portion thereof, and is not limited to the portion exemplified herein.

Further, one of skill in the art will understand, when armed with the present disclosure, that Kv1.3 deficiency encompasses no expression, insufficient and/or decreased expression, and/or the production of a non-functional Kv1.3, in that it does not exhibit the activity of Kv1.3 as disclosed herein.

The skilled artisan, once equipped with the teachings disclosed elsewhere herein, will readily appreciate how to produce transgenic animals deficient in Kv1.3. The skilled artisan will also appreciate, while recognizing that the disclosure contained herein is in no way limiting to the methods to produce a transgenic animal deficient in Kv1.3, that such animals can be produced by the deletion of the entire gene, or portions thereof. Further, the skilled artisan will appreciate that a transgenic animal deficient in Kv1.3 can be produced by introducing nonsense, missense, or other mutations in the coding regions of Kv1.3 gene. Further, one of skill in the art will appreciate that such animals can be generated by mutations in the promoter/enhancer region of the regulatory elements governing Kv1.3 expression. As disclosed elsewhere herein, methods to effect the expression of Kv1.3 can also encompass expression of an oligonucleotide antisense to the Kv1.3 gene, or some portion thereof, as well as the use of ribozymes and synthetic antibodies for the generation of a transgenic animal comprising a deficiency in Kv1.3. All such embodiments disclosed herein are encompassed in the present invention.

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

The following Examples can be summarized as follows. The present invention is based in part on the surprising discovery that the voltage-gated potassium channel Kv1.3 is a key molecule in the pathway involved in energy homeostasis, regulation of body weight, and insulin sensitivity. The data disclosed herein demonstrate that modulating the activity of Kv1.3, or its associated pathways, increases the resting metabolic rate, decreases mean caloric consumption, and as a result, leads to weight loss. Further, the data demonstrate that regulating/inhibiting Kv1.3 activity leads to both a lowering of blood glucose levels and an increase in insulin sensitivity and therefore, inhibition of Kv1.3 provides an effective means for the treatment of diabetes and obesity.

The present invention relates to the discovery that knockout mice deficient in Kv1.3 weigh about 18% less than age- and sex-matched controls, have an adipose tissue content that is approximately 350% lower than wild-type controls, and exhibit lower blood glucose levels and increased insulin sensitivity when compared to wild-type control animals.

Further, when selective Kv1.3 inhibitors were administered to wild-type mice, the mice displayed lower fasting blood glucose levels, increased insulin sensitivity, decreased food intake and a reduction in body weight compared with control animals.

Cultured muscle cells exhibited increased glucose uptake in the presence of a Kv1.3 inhibitor, and even greater glucose uptake in the presence of a Kv1.3 inhibitor and insulin. Additionally, mice deficient in Kv1.3 did not demonstrate any immunological dysfunction, serum electrolyte imbalances or other observable deleterious symptoms or phenotypes, such that the weight loss exhibited was not correlated with any non-specific toxicity due to deletion of the Kv1.3 allele.

The discovery that Kv1.3 plays an important role in glucose metabolism provides novel methods for treatment and prevention of diseases, disorders and conditions mediated by glucose metabolism, including, but not limited to diabetes, obesity, insulin resistance, hyerinsulinemia, Syndrome X, hypercholesterolemia, hyperlipoproteinemia, hypertriglyceridemia, artherosclerosis, glucose intolerance, diabetic nephropathy and the like. Thus, the present invention includes a method for treating obesity, or otherwise controlling weight, or for initiating weight loss in a mammal. The present invention also includes a method for controlling blood glucose levels and increasing insulin sensitivity in a mammal, which can be used to treat diabetes.

Generation of Kv1.3 deficient mice: Mice deficient in Kv1.3 (Kv1.3 (−/−) mice) were generated in the following manner. The Kv1.3 gene was isolated from a lambda FIX II 129/Ola library (Stratagene, La Jolla, Calif.) using a 238 base-pair Eco RI/Pst I 5' untranslated region of the mouse Kv1.3 cDNA to generate a probe. $^{32}$P incorporated probes ($^{32}$P-dCTP, Amersham Biosciences, Piscataway, N.J.) were prepared using a PRIME-IT II kit from Stratagene. Clone identity was confirmed using restriction mapping and sequencing.

Figure 3A:
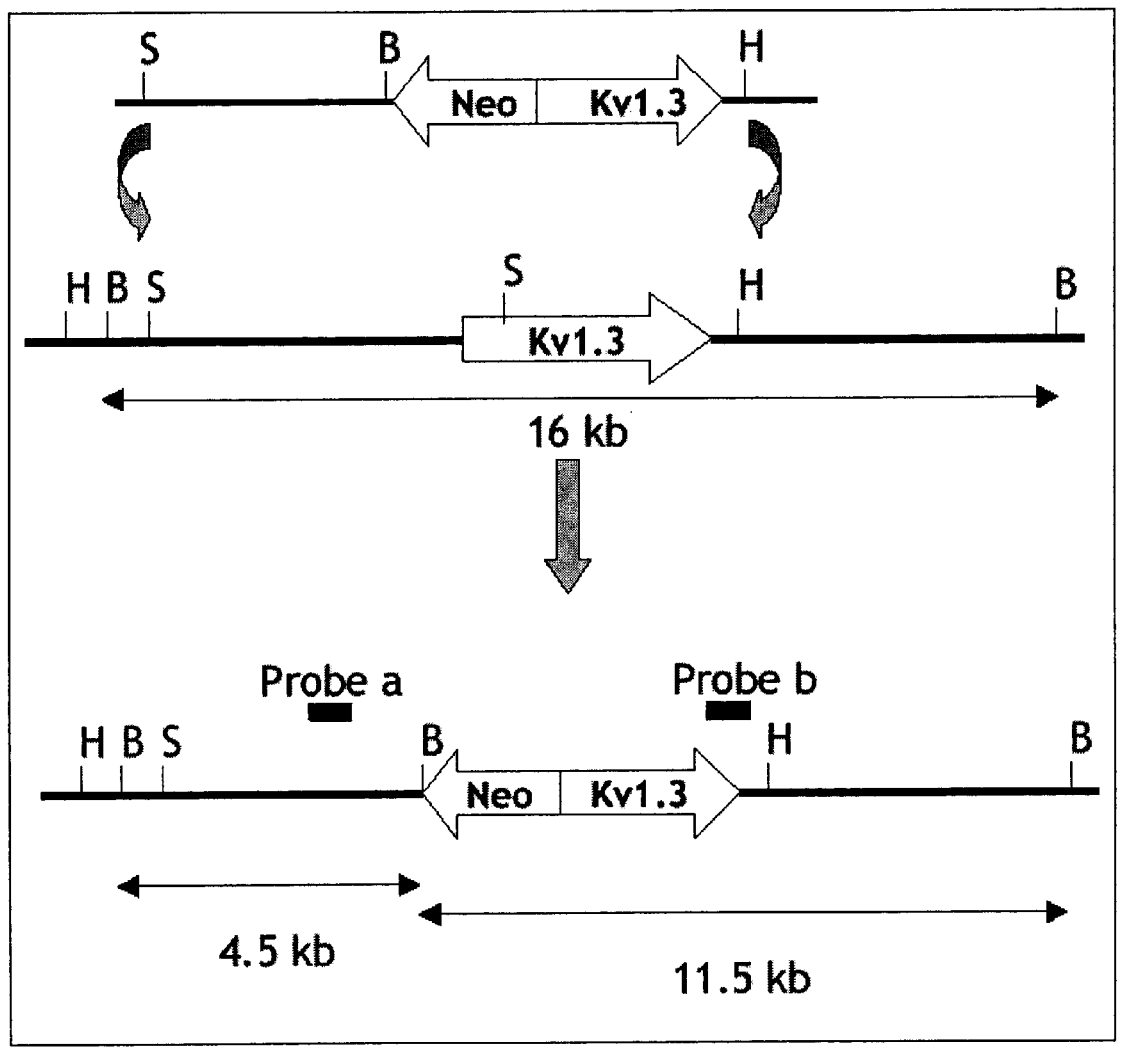
FIGS. 3A through 3C, depicts the targeting strategy and the generation of Kv1.3 (−/−) mice.
Figure 3B:
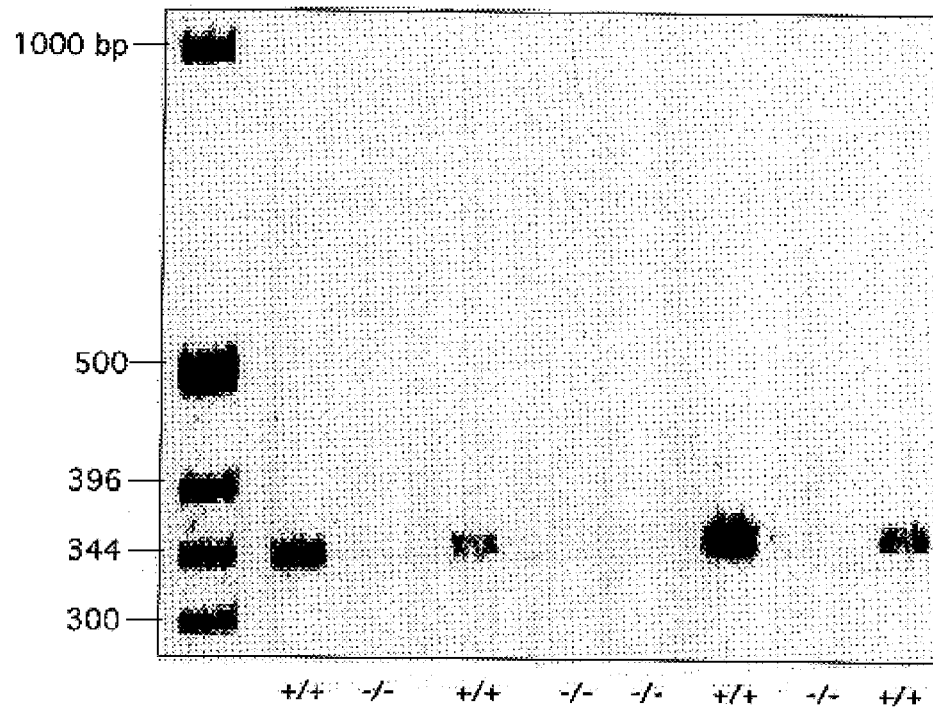
Figure 3C:
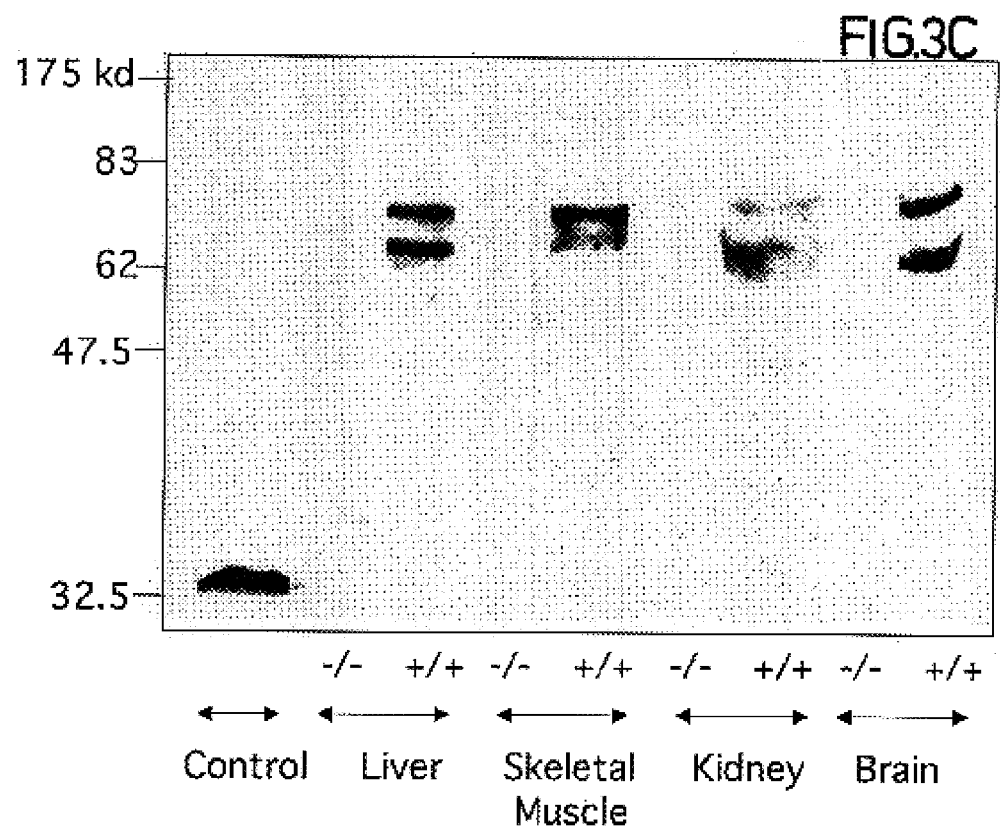

An 8.2 kb region spanning the upstream Bam HI site and the 3' Sal I site at the end of the lambda FIX II genomic clone was sub-cloned into pBluescript II (Stratagene). The Bam HI site was eliminated using Klenow polymerase and the construct was religated. The construct was then linearized using partial Xho I digestion and a herpes virus thymidine kinase (HSV-tk) gene cassette was inserted into the 3' end of the targeted region at the pBluescript Xho I site after Klenow end-filling, restoring the Hind III sites flanking the HSV-tk cassette. An Xho I/Sal I neomycin resistance cassette derived from pMC1neopA (Stratagene) was inserted into the 5' Xho I site in the opposite orientation of Kv1.3, thus regenerating the Xho I site downstream from the neomycin resistance cassette. The 1.8 kb Xho I/Sca I region of Kv1.3 was excised and the construct was religated after Klenow end filling. The left and right arms of the targeting construct are therefore 4.5 kb and 1.8 kb, respectively (FIG. 3A).

The targeting construct was linearized using Not I digestion and was introduced into mouse embryonic stem (ES) cells (ATCC, Manassas Va.) using electroporation (Hogan et al., 1986, Manipulating the Mouse Embryo: A Laboratory Manual, Cold Spring Harbor, N.Y.). ES cells were plated onto mitomycin C (Sigma Chemical Company, St. Louis, Mo.) treated primary embryonic fibroblasts. Double drug selection using 2 μM ganciclovir (Sigma Chemical Company) and 300 μg/ml G418 (Invitrogen, Carlsbad Calif.) was commenced 24 hours after the cells were plated. Probe A (a 1.5 kb Eco RI fragment) and Probe B (a 0.5 kb Hinc II/Sal I fragment at the 3' end of the genomic clone) were used in Southern Blots to screen ES cell colonies and potential transgenic mice (Sambrook et al., 1989, Molecular Cloning: A Laboratory Manual, Cold Spring Harbor Laboratory, New York; Hogan et al., 1986, Manipulating the Mouse Embryo: A Laboratory Manual, Cold Spring Harbor, N.Y.).

Homologous recombinant ES cells were injected into C57BL/6 blastocytes and chimeric males were bred to C57BL/6 females (Jackson Laboratories, Bar Harbor, Me.). Heterozygotes were interbred to obtain Kv1.3 deficient (Kv1.3 (−/−)) mice and wild type (WT) littermates as described in Hogan et al. (1986, Manipulating the Mouse Embryo: A Laboratory Manual, Cold Spring Harbor, N.Y.).

Kv1.3 deletion was confirmed using polymerase chain reaction and Western blotting. A 5' primer, ATACTTCGAC-CCGCTCCGCAATGA (SEQ ID NO:1) and a 3' primer, GCAGAAGATGACAATGGAGATGAG (SEQ ID NO:2) specific for Kv1.3 were used to amplify genomic DNA templates. The PCR cycle (35 cycles) was as follows: denaturing for 1 minute at 94° C., annealing for 2 minutes at 55° C., and extension for 3 minutes at 68° C. The PCR product was resolved using a 1% agarose gel and transferred to a nitrocellulose membrane. The membrane was probed with $^{32}$P labeled cDNA as described elsewhere herein.

For Western blotting, homogenates were prepared from liver, skeletal muscle, kidney, and brain of Kv1.3 (−/−) and Kv1.3 (+/+) mice. Proteins (10 μg) were resolved using SDS-PAGE and transferred to nitrocellulose membranes (Laemmli et al., 1970, Nature 227:680–685). Membranes were probed using a rabbit anti-human Kv1.3 polyclonal antibody (1:200, Alomone, Israel) per the manufacturer's instructions. A positive control provided by the manufacturer was run as well.

Measurement of Kv1.3 (−/−) Immunological Function and Electrophysiology

Fluorocytometry

Cells were recovered into 10 ml Bruff's/5% fetal calf serum (FCS) from thymus, spleen and/or mesenteric lymph nodes by using the plunger of a syringe to tease the tissues between two pieces of 0.1 mm nylon mesh (Small Parts, Inc., Miami Lakes, Fla.). Splenocytes were centrifuged at 1000 rpm at 4° C. for 5 minutes, re-suspended in 2 ml of erythroid cell lysis buffer (Biofluids, Rockville, Md.) and then made up to 10 ml with PBS. All cell suspensions were then filtered through the 0.1 mm nylon mesh and centrifuged at 1000 rpm in a bench top centrifuge at 4° C. for 5 minutes. Finally, cells were re-suspended in 10 ml Bruffs/5% FCS for counting in a hemocytometer.

Aliquots of $10^6$ cells were made into 0.2 ml PBS/1% FCS supplemented with 5 mg/ml FcBlock (PharMingen, San Diego, Calif.). Samples were left on ice for 30 minutes before primary antibodies were added and left on ice in the dark for a further 1 hour. Samples were washed in 1.2 ml PBS/1% FCS before centrifugation at 1000 rpm at 4° C. for 5 minutes. Secondary antibody incubation and washing were done as above. Four-color fluorocytometry employed a FACSCalibur with argon and helium-neon lasers (Becton Dickinson, San Jose, Calif.). Data were analyzed with CellQuest software (provided by the manufacturer) by first gating on lymphocytes/lymphoblasts, based on forward and side scatter. PharMingen antibodies and other reagents used included anti-IgD (clone 11-26c.2a)-FITC, anti-ab TCR (clone H57-597)-biotin, anti-CD3e (clone 2C11)-FITC, anti-CD4 (clone RM4-5)-allophycocyanin (APC), anti-CD8a clone 53-6.7)-APC, anti-CD24 (clone M1/69)-biotin, anti-CD44 (clone IM7)-Cy-Chrome, anti-CD45R (B220, clone RA3-6B2)-Cy-Chrome, anti-CD45R (B220, clone RA3-6B2)-phycoeythrin (PE), anti-CD62L (clone Mel-14)-PE, streptavidin-Cy-Chrome, streptavidin-PE and annexin V-PE. Anti-mouse IgM (donkey polyclonal)-Cy5 was from Jackson Immunochemicals Inc. (West Grove, Pa.). Other reagents used were DiOC6 (Molecular Probes, Eugene, Oreg.) and 7-amino actinomycin D (7-AAD) (Calbiochem, San Diego, Calif.).

Apoptosis Assays

Thymocytes were prepared in Bruff's/5% FCS as above and used in two types of apoptosis assays. In one assay, aliquots of $10^6$ cells/ml were treated with 1 mM dexamethasone (Sigma), 2 mM staurosporine (Clontech, Palo Alto, Calif.) or medium alone in 24-well plates in a 37° C., 5% CO2 incubator for 6 hours. Alternatively, aliquots were treated with 10 mg immobilized anti-CD3 antibody (clone 72C 11; grown in-house, Harlow et al., 1988, Antibodies: A Laboratory Manual, Cold Spring Harbor, N.Y.), 10 mg immobilized anti-Fas antibody (clone Jo2; PharMingen) or medium alone in 24-well plates for 24 h as above. Ultraviolet light (u.v.) treatment was for 5 minutes on a standard transilluminator followed by culturing for 24 hours.

Thymocytes were then centrifuged at 1000 rpm for 5 minutes and resuspended in 0.1 ml annexin V-staining buffer (PharMingen) containing 1 mg/ml 7-AAD (Calbiochem), 20 mg/ml annexin V-PE (PharMingen) and 20 mM DiOC6 (Molecular Probes). Samples were then left at room temperature in the dark for 20 minutes before being made up to 0.5 ml with annexin V-staining buffer for fluorocytometry, as above. Percentages of thymocytes that were 'live' (7-AAD-low), annexin-V (Ann) positive or negative and $DiOC_6$ positive or negative were then determined from the fluorocytometry data and represented as mean percentage of thymocytes±standard deviation (SD) from three mice per group.

T Cell Stimulation Assays

Splenocytes were prepared in Bruff's/5% FCS as described above and 0.2 ml of $5\times10^5$ cell aliquots placed in 96-well plates. Cells were cultured in a 37° C., 5% CO2 incubator with or without 1–30 µg/ml Concanavalin A (Boehringer Mannheim) or 0.1 mg/ml anti-CD3 (2C11). After 48 h, 1 mCi $H^3$-thymidine (Perkin Elmer Life Sciences, Boston, Mass.) was added to each well for a further 16 h. Thymidine incorporation was then determined with a Wallac plate cell harvester and scintillation counter (Perkin Elmer Life Sciences, Boston, Mass.).

Chemicals and Solutions

All salts and buffers were purchased from Sigma Chemical Co. St. Louis, Mo., as were several ion-channel blockers: the Cl--channel blockers, 4-nitro-2-(3 phenylpropylamino)-benzoic acid (NPPB) and 4,4'-diisothiocyanatostilbene-2,2'-disulfonic acid (DIDS), and the K+-channel blocker tetra-ethylammonium (TEA). Agitoxin-2 (AgTx-2) was from Alomone Labs, Israel. Stock solutions of NPPB (500 mM) and DIDS (500 mM) were dissolved in DMSO and stored at −20° C. When DMSO was used as the solvent, the maximal final concentration in the bathing solution was about 0.2%. Thus, control recordings included 0.2% DMSO in the bath solution. Stock solutions of AgTx-2 (1 mM) and ChTx (50 mM) were made in standard bath medium (see below) supplemented with 0.1% bovine serum albumin (BSA, Sigma) to prevent adhesion to surfaces, and stored at −20° C. Control recordings were done by adding 0.1% BSA to the bath solution.

Patch-clamp Electrophysiology

Thymocytes were prepared as above and then washed 5 times in RPMI 1640/L-glutamine, supplemented with 10% FCS (all from Gibco BRL). Whole-cell currents were measured using an Axopatch 200 amplifier and pCLAMP version 6.04 software (both from Axon Instruments, Union City, Calif.). Patch electrodes of resistance 8–12 MΩ were pulled from thick-walled borosilicate glass (World Precision Instruments, Sarasota, Fla.). During data acquisition, capacitive currents were canceled by analog subtraction, and all currents were filtered at 2 kHz via the amplifier. Data analysis was performed using pCLAMP and Origin (version 5, Microcal Software, Northhampton, Mass.), and curve fitting used the iterative Levenberg-Marquardt algorithm of non-linear regression. All recordings were made at room temperature (18–21° C.). All data were corrected for junction potentials between bath and pipette solutions. The standard bathing solution contained (mM): 145 NaCl, 5 KCl, 1 MgCl2, 1 CaCl2, 5 HEPES, adjusted with NaOH to pH 7.4. The standard pipette solution contained (mM): 145 K aspartate, 1 $K_4$BAPTA, 5 HEPES, 1 $MgCl_2$, 0.09 $CaCl_2$, 2 $K_2$ATP, adjusted to pH 7.2 with KOH. The resulting low $Ca^{2+}$ (10 nM) pipette solution allowed $Cl^-$ currents and voltage-gated $K^+$ currents to be monitored without contaminating $Ca^{2+}$-activated currents. Fresh $K_2$ATP (Sigma) was added to pipette solutions just before use to help maintain channel activity during whole-cell recording. Occasionally, to isolate $K^+$ currents, $Cl^-$ currents were reduced by substituting aspartate for most of the $Cl^-$ in the bath.

Measurement of Kv1.3 (−/−) mouse metabolic activity: Female age-matched Kv1.3 (−/−) (n=5) and control mice (n=5) were housed in metabolic cages. Food intake, weight, and urine output were monitored for 35 days. Male Kv1.3 (−/−) and control mice (n=9 for each group) were fed a high fat diet (F3282, 35.5% fat, BioServ, Inc., Frenchtown, N.J.) and weights were determined at the indicated intervals.

Plasma insulin and glucose levels and insulin sensitivity assay in Kv1.3 (−/−) and control mice: Age-matched Kv1.3 (−/−) and control mice fasted for 12 hours. Blood glucose levels were measured using a GLUCOMETER™ (Bayer Corp., West Haven, Conn.). Mouse plasma insulin levels were measured using a radio-immunoassay at Linco Research, Inc. (St. Charles, Mo.). Human insulin was administered by intraperitoneal (IP) injection ($7.5\times10^{-4}$ U/gram body weight) to non-fasting, age-matched Kv1.3 (−/−) and wild-type mice (n=11 for each group) at time=0. Blood glucose levels were measured at various time intervals.

Plasma insulin levels and insulin sensitivity: Seven-week old C57BL6/6J male mice (n=5) were given 0.1 µg/gram body weight margatoxin 20 hours prior to study via IP injection. Controls (n=5) were sham injected with phosphate buffered saline (PBS). Two hours prior to study a second injection of margatoxin was administered to the treated experimental group. At t=0, both groups received human insulin as described previously. Blood glucose measurements were performed at the times indicated.

Non-fasting ob/ob (obese) mice (n=5), were given margatoxin 30 minutes prior to study as described elsewhere herein. Age-matched control ob/ob mice were sham injected with PBS. Both groups were given human insulin and blood glucose levels were monitored as described previously.

Non-fasting ob/ob (obese) mice (n=5), were given kaliotoxin (Alomone, Israel) 30 minutes prior to study as described elsewhere herein. Age-matched control ob/ob mice were sham injected with PBS. Both groups were given human insulin and blood glucose levels were monitored as described previously.

Fasting db/db (diabetic) mice (n=5), were given margatoxin 30 minutes prior to study as described elsewhere herein. Age-matched control db/db mice were sham injected with PBS. Both groups were given human insulin and blood glucose levels were monitored as described previously.

Measurement of resting metabolic rates, body fat content and physical parameters: Metabolic rate was measured by indirect calorimetry using an open, four-chamber Oxymax System (Columbus Instruments, Columbus Ohio) per the manufacturer's instructions. $O_2$ consumption and $CO_2$ production were measured every 40 minutes for 4 hours between 11 a.m. and 3 p.m. for two consecutive days and the results were averaged. Heat production was calculated and expressed per gram body weight (cal/hr/gram body weight). Total physical activity was measured using the optical beam technique using an Opto-Varimex Mini (Columbus Instruments, Columbus Ohio) per the manufacturer's instructions.

Whole body composition was analyzed using Dual X-ray Absorptiometry (DEXA, PIXImus, GE-Lunar, Waukesha, Wis.). Accuracy was determined using controls of known values. Total body analysis was acquired over a 5 minute period, and the data were analyzed using software provided by the manufacturer.

Long-term pharmacological inhibition of Kv1.3: Ob/ob mice were injected intraperitoneally with margatoxin or PBS (n=5 for each group) on days 0, 5, and 16 as described herein. Food consumption was monitored for 30 days, and weights were measured at the end of 30 days.

Kv1.3 detection in L6 cells: Rat skeletal muscle cells (L6 cells, ATCC, Manassas, Va.) were assayed for the presence of Kv1.3. cDNAs were synthesized from RNA extracted from L6 cells and PCR was used to detect KKv1.3 DNA as previously described.

D-glucose uptake in L6 cells: L6 cells were maintained in Dulbecco's Modified Eagle's Medium (DMEM) containing 10% fetal bovine serum (FBS) and 1% penicillin-streptomycin in T-75 flasks at 37° C. and 5% $CO_2$. To promote fusion into myotubules and quiescence, L6 cells were seeded onto 10 cm² flasks at a density of 3000 cells/cm² in DMEM containing 2% FBS. Myotube formation was determined by the percentage of nuclei in multinucleated cells. Glucose uptake assays were performed when 80–90% of the myoblasts fused into myotubes. Cells were serum starved for 3 hours in DMEM containing 0.2% bovine serum albumin, washed twice in PBS with 0.1 mM $CaCl_2$, 0.1 $MgCl_2$, 10 mM HEPES, pH 7.4. Cells were incubated in KRPH (118 mM NaCl, 5 mM KCl, 1.3 mM $CaCl_2$, 1.2 mM $MgSO_4$, 1.2 mM $KH_2PO_4$, and 30 mM HEPES, pH 7.4) containing 0.2–250 nM margatoxin and/or 0.1 nM insulin at 37° C. 2-deoxy-($^3$H)D-glucose (1 µCi/ml, 10 µM/liter) uptake was measured in triplicate over a 10 minute period. The reaction was terminated by washing with ice-cold PBS. Non-specific uptake was determined by adding 10 mM phloretin and was subtracted from total uptake. Cells were lysed in 0.1 N KOH, and glucose uptake was measured by liquid scintillation (Packard BioScience, Meriden Conn.). Protein uptake was measured by Bradford Assay.

The results of the experiments presented in this Example are now described.

Breeding results and phenotype of Kv1.3(−/−) mice: PCR amplification of wild type versus Kv1.3(−/−) genomic DNA showed a 340 bp band in wild type mice that was absent in Kv1.3(−/−) mice. Western blotting results demonstrated a 68–72 kDa band in wild type mice, but not in Kv1.3(−/−) mice, further confirming knockout of the Kv1.3 gene.

When maintained on a normal diet, Kv1.3 (−/−) mice were born at a normal Mendelian ratio, and did not exhibit any differences in gross appearance, lack of breeding, or reduced litter size when compared to Kv1.3 (+/+) or Kv1.3 −/+ littermates. Further, Kv1.3(−/−) mice have no detectable immune deficiencies, and do not require special breeding or housing conditions. Kv1.3(−/−) mice exhibit no difference in life span as compared to control mice.

As shown in Table 1 and Table 2, Kv1.3(−/−) mice have a significantly higher resting metabolic rate, a significantly lower body weight, but similar body fat percentages and overall length as wild type controls.

TABLE 1

| | Male Kv1.3(+/+) | Male Kv1.3(−/−) | Significance (p) |
|---|---|---|---|
| Weight (grams) | 26.84 ± 0.99 | 23.53 ± 0.36 | p < 0.003 |
| % Body Fat (DEXA) | 28.16 ± 2.08 | 24.90 ± 1.18 | Not Significant |
| Body Length (cm) | 9.2 ± 0.09 | 9.07 ± 0.02 | Not Significant |
| Total Activity (counts/hr) | 917.0 ± 96 | 794.0 ± 57 | Not Significant |
| Metabolic Activity (cal/hr/gram BW) | 11.8 ± 0.31 | 13.9 ± 0.39 | p < 0.0005 |

TABLE 2

| | Female Kv1.3((+/+)) | Female Kv1.3(−/−) | Significance (p) |
|---|---|---|---|
| Weight (grams) | 19.90 ± 0.64 | 18.30 ± 0.64 | p < 0.003 |
| % Body Fat (DEXA) | 21.56 ± 3.69 | 19.32 ± 1.56 | Not Significant |
| Body Length (cm) | 8.47 ± 0.05 | 8.31 ± 0.07 | Not Significant |
| Total Activity (counts/hr) | No Data | No Data | No Data |
| Metabolic Activity (cal/hr/gram BW) | No Data | No data | No Data |

Kv1.3 (−/−) mice have normal serum electrolytes: Kv1.3 is expressed in the kidneys, amongst other places, and therefore may play a role in potassium secretion (Yao et al., 1996, J. Clin. Invest. 97:2525–2533). Moreover, recent evidence has demonstrated Kv1.3 mRNA is upregulated by almost ten-fold when stimulated by serum/glucocorticoids/induced/kinase (SGK), suggesting a role for Kv1.3 in renal sodium conservation (Warntges et al., 2002, Pflugers Arch. 443:617–624). To this end, serum electrolyte levels were measured in Kv1.3 (−/−) mice. As shown in Table 3 and Table 4, there were no significant differences between Kv1.3 (−/−) mice and controls, suggesting the Kv1.3 deficiency does not cause any observable alterations in the ability of the renal system to process sodium or potassium.

TABLE 3

| | Urine Output | Urinary Electrolytes (mmol/day) | | |
|---|---|---|---|---|
| | (ml/day) | Na | K | Cl |
| Kv1.3(+/+) | 0.65 ± 0.08 | 0.16 ± 0.015 | 0.32 ± 0.04 | 0.28 ± 0.03 |
| Kv1.3(−/−) | 1.11 ± 0.21 | 0.19 ± 0.022 | 0.44 ± 0.03 | 0.42 ± 0.03 |

TABLE 4

| | Serum Electrolytes (meq/L) | | | |
|---|---|---|---|---|
| | Na | K | Cl | $HCO_3$ |
| Kv1.3(+/+) | 149 ± 2.25 | 4.8 ± 0.16 | 110 ± 0.87 | 21.03 ± 1.1 |
| Kv1.3(−/−) | 147 ± 1.36 | 5.15 ± 0.18 | 109 ± 0.68 | 20.1 ± 0.57 |

Figure 4:
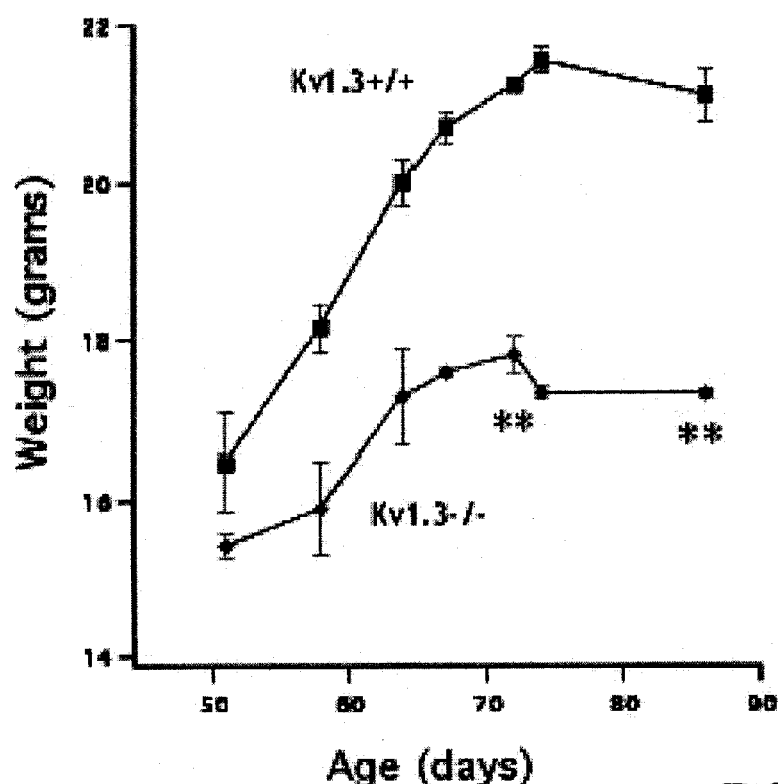
FIG. 4 is a graph depicting the weight of female wild type and Kv1.3 (−/−) mice over time.
Figure 5:
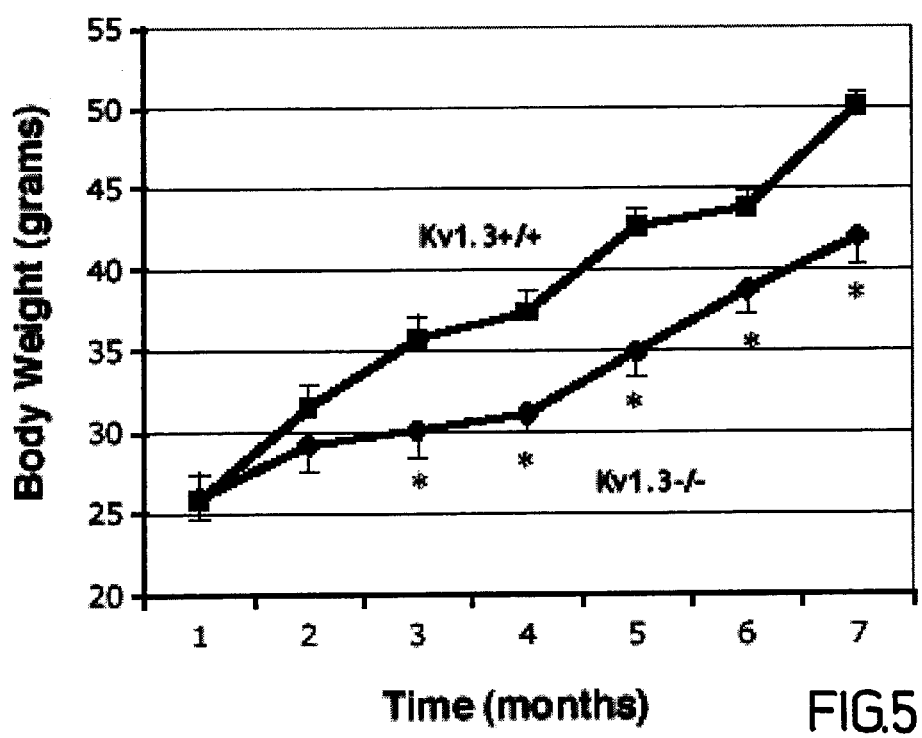
FIG. 5 is a graph depicting the weight of male wild type and Kv1.3 (−/−) mice fed a high fat diet over a period of seven months.

Kv1.3 (−/−) mice eat less and weigh less: The food intake, weight, and urine output of Kv1.3(−/−) and control mice housed in metabolic cages was monitored for one month. Kv1.3 (−/−) mice ate less than age- and sex-matched control mice (2.83±0.2 grams/day versus 3.52±0.3 grams/day, respectively, p<0.003). Importantly, there were no significant differences in urine output between the two groups. At three months, Kv1.3 (−/−) mice weighed significantly less (18%) than age- and sex-matched controls (FIG. 4). Weight loss was not restricted to female mice, as male Kv1.3 (−/−) mice raised on a high fat diet weighed significantly less than control mice at 7 months (FIG. 5).

Kv1.3 (−/−) mice have lower body fat than controls: White adipose tissue content is lower in Kv1.3 (−/−) mice than in control mice. The epididymal fat pad of control mice (body weight=33.85 grams, fat pad weight=0.746 grams, testes weight=0.120 grams) weighs 350% more than in Kv1.3(−/−) mice (body weight=27.66 grams, fat pad weight=0.210 grams, testes weight=0.116 grams).

Figure 6B:
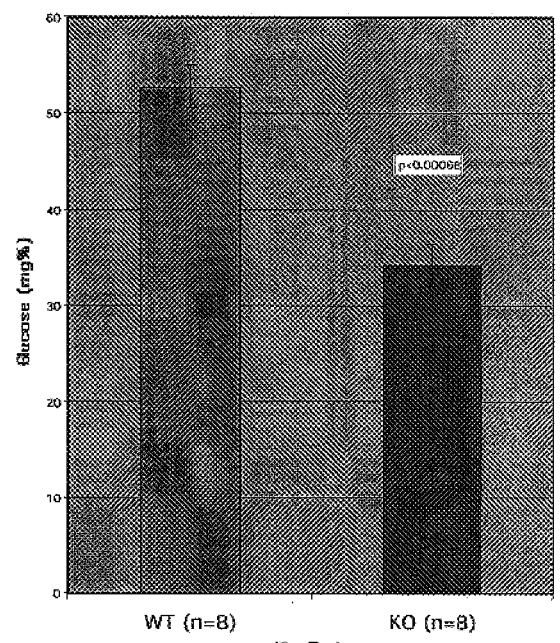
FIGS. 6A and 6B, is a series of graphs depicting plasma insulin and glucose levels in wild type and knockout mice.
Figure 6A:
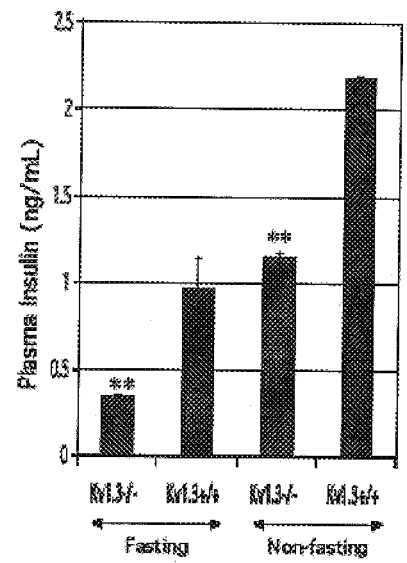
Figure 7:
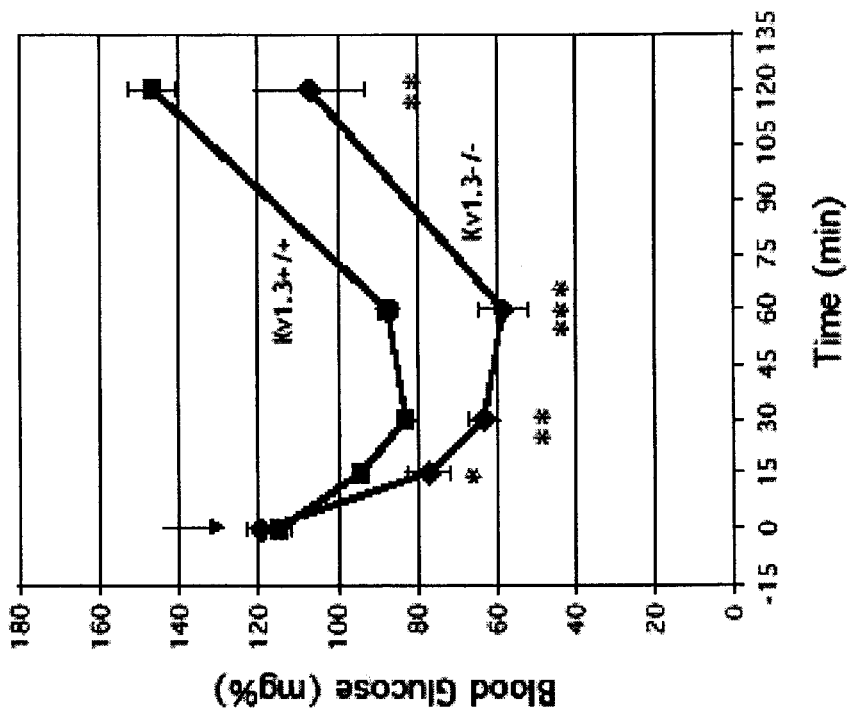
FIG. 7 is a graph depicting insulin tolerance in non-fasting, age-matched (5 months) Kv1.3 (−/−) and wild type control mice. (*) indicates a p value of <0.05, () indicates a p value of <0.01, and (*) indicates a p value of <0.003.

Kv1.3 (−/−) mice demonstrate lower fasting blood glucose and insulin concentration, and increased insulin sensitivity: After an overnight fast, Kv1.3(−/−) mice have significantly lower blood glucose levels than their wild type counterparts (FIG. 6). Additionally, Kv1.3(−/−) mice demonstrated significantly increased sensitivity to insulin as compared with wild type controls (FIGS. 7A and 7B).

Figure 8:
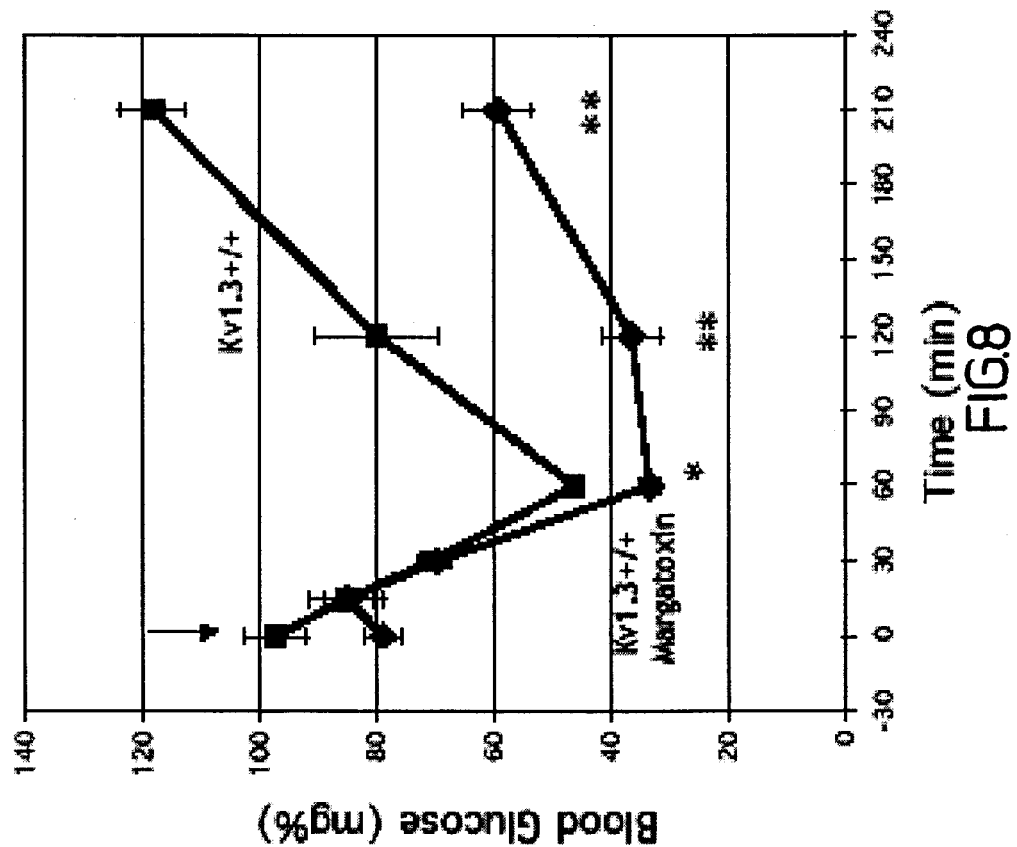
FIG. 8 is a graph depicting the effect of margatoxin (a voltage-gated potassium channel inhibitor) on insulin sensitivity in fasting, age-matched C57BL/6 mice (wild type) mice over time. Experimental treated mice (squares) were injected with 0.1 μg/gram margatoxin at t=−20 hours and again at t=−2 hours. Control mice (diamonds) were given phosphate buffered saline (PBS) at the same times. Human insulin was administered intraperitoneally (7.5×10$^{-4}$ gram/gram body weight) at t=0, and blood glucose was monitored at the times indicated. (*) indicates a p value of <0.05, (**) indicates a p value of <0.01.
Figure 10:
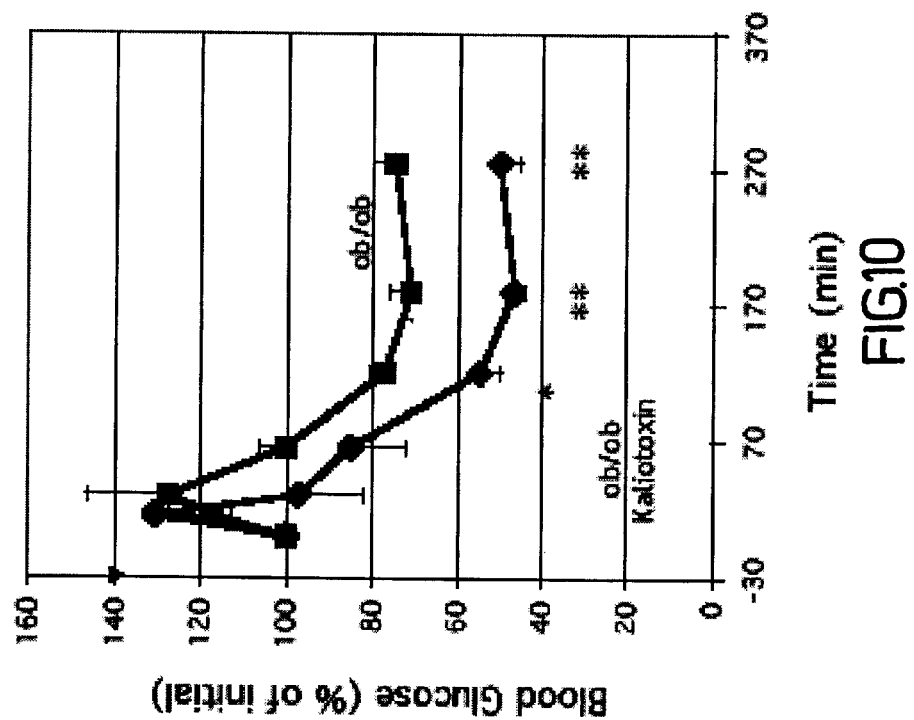
FIG. 10 is a graph depicting the effect of kaliotoxin (a voltage-gated potassium channel inhibitor) on non-fasting, age matched (2.5 month old) ob/ob mice. Experimental mice (squares) were given 0.1 μg/gram margatoxin at t=−30 minutes intraperitoneally. Control mice (diamonds) were sham injected with PBS only. At t=0, human insulin was administered (7.5×10$^{-4}$ gram/gram body weight) and blood glucose was monitored at the times indicated.
Figure 9:
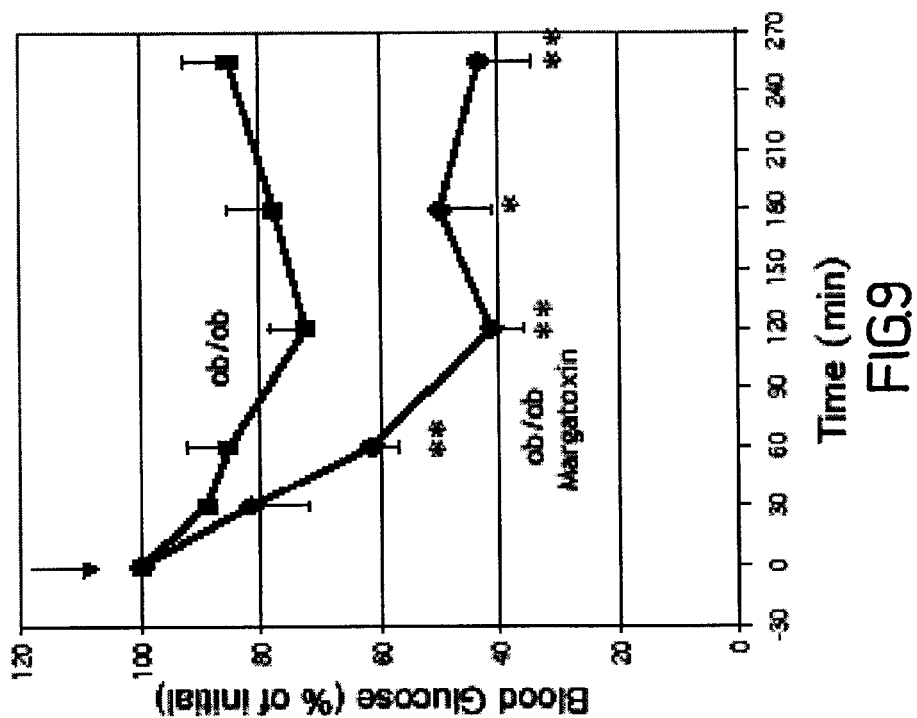
FIG. 9 is a graph depicting the effect of margatoxin on non-fasting, age matched (4 month old) ob/ob mice, an art-recognized model for human obesity. Experimental mice (diamonds) were given 0.1 μg/gram margatoxin at t=−30 minutes intraperitoneally. Control mice (squares) were sham injected with PBS. At t=0, human insulin was administered (7.5×10$^{-4}$ gram/gram body weight) and blood glucose was monitored at the times indicated. (*) indicates a p value of <0.05, (**) indicates a p value of <0.01.
Figure 11:
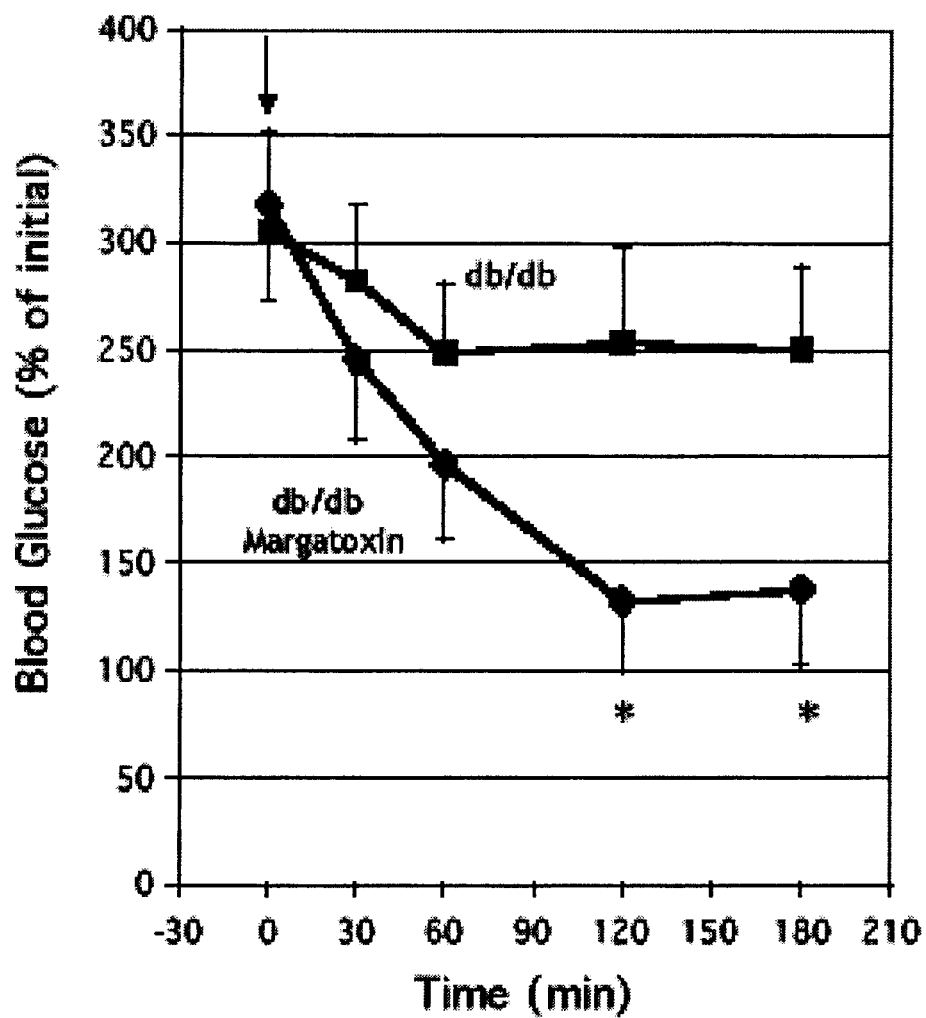
FIG. 11 is a graph depicting the effect of margatoxin on fasting, age-matched db/db mice, an art-recognized model for human diabetes. Experimental mice (diamonds) were given 0.1 μg/gram margatoxin at t=−30 minutes intraperitoneally. Control mice (squares) were sham injected with PBS. At t=0, human insulin was administered (7.5×10$^{-4}$ gram/gram body weight) and blood glucose was monitored at the times indicated. (*) indicates a p value of <0.05, (**) indicates a p value of <0.01.

Pharmacological inhibition of Kv1.3 results in increased insulin sensitivity: Margatoxin administered to C57BL/6 mice resulted in an increased insulin sensitivity when compared to controls given sham injections (FIG. 8). Similarly, margatoxin and kaliotoxin, another voltage-gated potassium channel inhibitor, significantly increased insulin sensitivity in ob/ob mice (FIGS. 9 and 10). Additionally, db/db mice treated with margatoxin showed a significant increase in sensitivity to insulin (FIG. 11).

Figure 12:
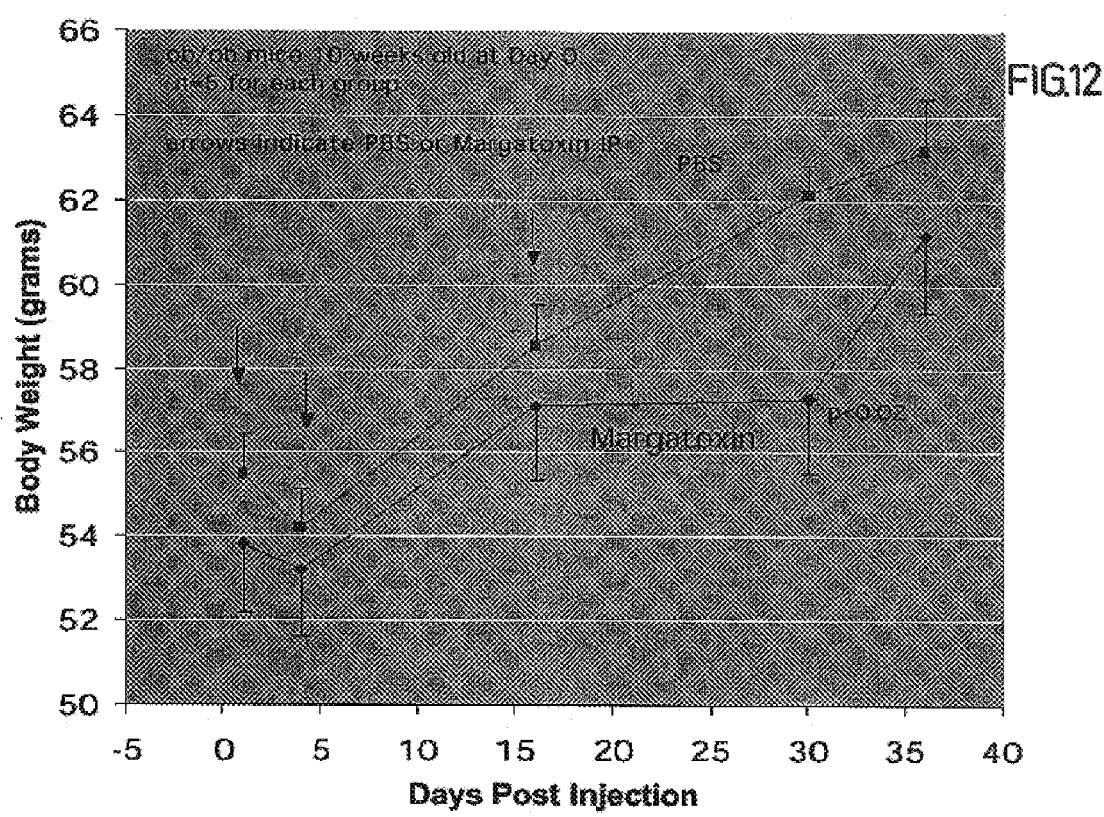
FIG. 12 is a graph depicting the effect of long-term Kv1.3 inhibition on body weight in ob/ob mice. Age-matched mice (10 weeks old) were given 0.1 μg/gram margatoxin intraperitoneally (diamonds) or PBS (squares) at days 0, 5, and 16 (indicated by arrows). Both groups were fed identical amounts at identical times, and body weights were assessed on days 0, 5, 16 and 36. Margatoxin treatment ceased at day 16, and the experimental mice began to gain weight thereafter.

Margatoxin treated mice eat less and weigh less than controls: Ob/ob mice treated long term with margatoxin ate significantly less than controls (0.62±0.004 versus 0.104±0.01 grams/gram body weight/day respectively, p<0.02). Further, ob/ob mice treated long term with margatoxin weighed significantly less than controls (FIG. 12).

Figure 13:
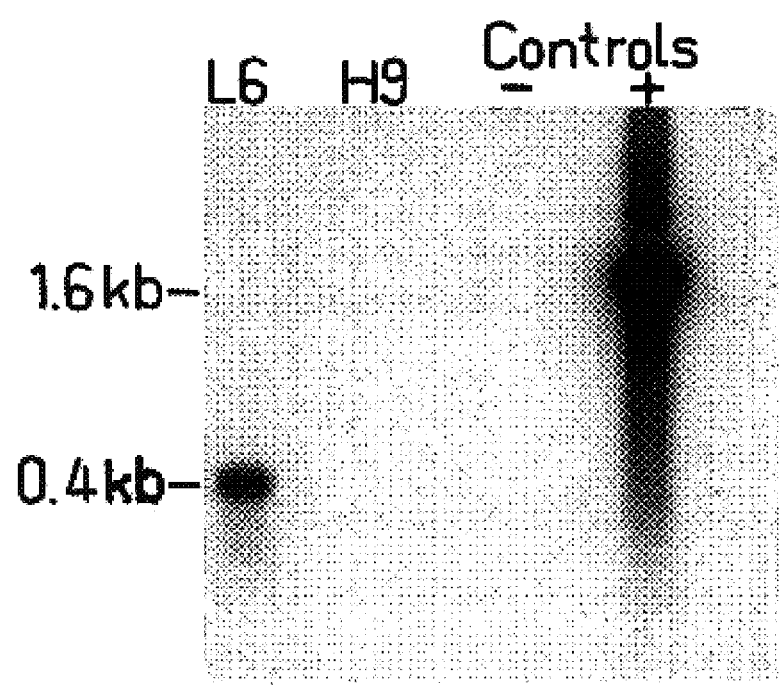
FIG. 13 is an image depicting a Southern blot demonstrating the presence of nucleic acid encoding Kv1.3 in L6 muscle cells.
Figure 14:
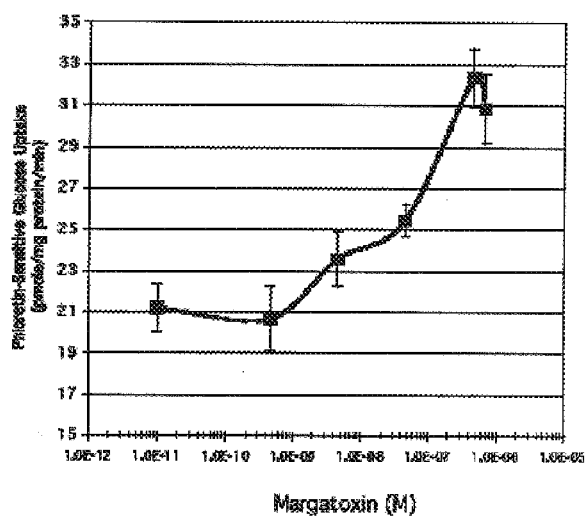
FIG. 14 is a graph depicting the dose-dependent response of glucose uptake in L6 cells administered margatoxin.
Figure 15:
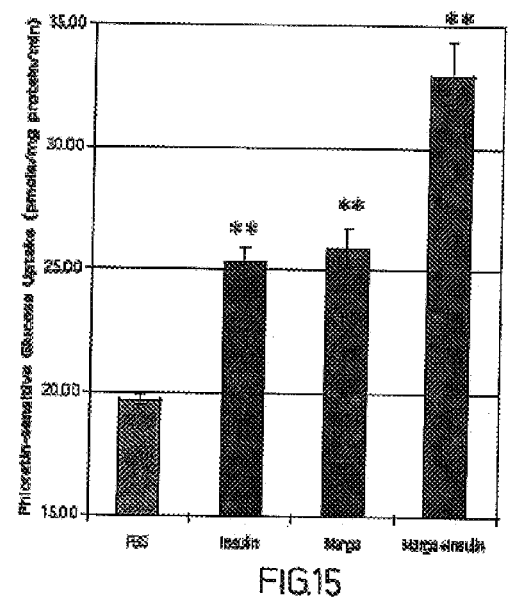
FIG. 15 is a graph that depicts the effects of margatoxin and insulin, alone or in combination, on glucose uptake in L6 muscle cells, (**) indicates a p value of <0.01.

Margatoxin increases glucose uptake in muscle cells: L6 rat muscle cells express the Kv1.3 gene (FIG. 13). Pharmacological inhibition of Kv1.3 with margatoxin increases uptake of glucose in L6 cells in a dose dependent manner (FIG. 14). L6 cells incubated with 200 nM insulin and 250 nM margatoxin exhibited significantly increased glucose uptake when compared to cells incubated with margatoxin of insulin alone, or cells incubate with neither (FIG. 15).

Discussion

Voltage-gated potassium (Kv) channels are a diverse group of membrane proteins that participate in the regulation of the cell membrane potential and modulate a variety of cellular functions. Kv1.3, a member of the Shaker family of Kv channels, is found in many tissues, including kidney (Yao et al., 1996, J. Clin. Invest 97:2525–2533) lymphocytes (Cahalan et al., 1991 Current Topics in Membranes 39:357–394; Ghanshani et al., 2000, J. Biol. Chem. 275:37137–37149; Levite et al., 2000, J. Exp. Med. 191:1167–1176), CNS (Mourre et al., 1999, J. Pharm. Exp. Ther. 291:943–952), liver, skeletal muscle, testis and spermatozoa (Jacob et al., 2000, Mol. Hum. Reprod. 6: 303–313), osteoclasts (Arkett et al., 1994, Receptors Channels 2: 281–293), and is believed to participate in a variety of cellular functions including apoptosis, cell volume regulation and T cell stimulation (Lang et al., 1999, Herz. 24: 232–235; Kalman et al., 1998, J. Biol. Chem. 49: 32697–32707). It is, to date, the only potassium channel shown to be regulated by serum-glucocorticoid activated kinase (SGK), one of the main mediators of aldosterone action at the renal distal tubule (Warntges et al., 2002, Pflugers Arch. 443: 617–624). Protein Kinase C (PKC) increases (Chung et al., 1997, J. Membr. Biol. 156: 73–85) and tyrosine kinase (TK) inhibits Kv1.3 channel activity (Fadool et al., 2000, Neurophysiol 83–2332–2348). In olfactory bulb neurons, where Kv1.3 mediates a large proportion of the measured outward current (Fadool et al., 1998, J. Neurosci 18:6126–6137), its activity is down-regulated by insulin through activation of receptor tyrosine kinase.

To elucidate the role of Kv1.3 in vivo, we generated Kv1.3 -deficient mice by disrupting the Kv1.3 locus using homologous recombination. Gene disruption was confirmed by PCR, and Western blotting. The expected Mendelian ratio was observed for mice born from the mating of heterozygous parents, newborn Kv1.3 (−/−) mice appeared normal, required no specific precautions for survival and growth and were indistinguishable from wild type littermates in terms of appearance and behavior.

Kv1.3 (−/−) animals consistently weighed less than littermate controls when female mice were observed in metabolic cages for up to 35 days. The weight difference was also noted in pair-fed mice. Body lengths were indistinguishable, as was bone structure assessed by dual energy X-ray absorptiometry scan (DEXA) (Yale Core Center for Musculoskeletal Disorders, P30AR46032). Although total body fat content estimated by DEXA was lower in Kv1.3 (−/−), the difference did not reach statistical significance (Table 1). Since body weight is controlled largely by energy intake and expenditure, to further elucidate the role of Kv1.3 in body weigh regulation, we measured caloric intake, metabolic rate and activity levels in Kv1.3-deficient mice. While food intake was similar in Kv1.3−/− and control mice, resting metabolic rate (measured from 11 AM–3 PM) was significantly higher in Kv1.3 (−/−) mice. Interestingly, while Kv1.3 (−/−) mice were as active as controls at baseline, they exhibited a significant increase in total activity during their wakeful period (11 PM–1 AM). This may partly account for the increased in basal metabolic rate observed at rest. Kv1.3 (−/−) mice also gained less weight than controls when fed a high fat diet. The difference in weight gain was evident by the second month, reached statistical significance by month 3 and persisted until the end of the observation period in both male and female mice. Based on the above, we conclude the weight reduction observed in Kv1.3-deficient mice is primarily due to increased metabolic rate. Since Kv1.3 is highly expressed in hypothalamus (Mourre et al., 1999, J. Pharmacol Exp. Ther., 291:943–952) and channel activity is inhibited by serotonin (Attali et al., 1992, FEBS Lett., 303–229–232), it could modulate sympathetic nerve system output, and metabolic rate.

Since body weight, and fat content are important regulators of peripheral insulin sensitivity we examined the effect of Kv1.3 deletion on glucose metabolism. Although Kv1.3 (−/−) and wild type mice had similar glucose levels, fasting and non-fasting plasma insulin concentrations were significantly lower in Kv1.3 deficient animals. Glucagon levels were not significantly different. An insulin tolerance test confirmed that Kv1.3−/− mice were more sensitive to the actions of insulin. Indeed, insulin caused a significantly greater fall in blood glucose of Kv1.3 (−/−) mice, starting 15 minutes post injection and lasting at least 2 hours. Taken together, the data suggest that disruption of the Kv1.3 gene is associated with an apparent increase in insulin sensitivity. Several mechanisms could account for this observation, including decreased glucose production by liver or increased glucose uptake by skeletal muscle. Furthermore, Kv1.3 deletion could modulate insulin-independent glucose uptake.

While inhibition of Kv1.3 currents potentiates the hypoglycemic action of insulin, the role of compensatory mechanisms activated by the chronic and complete absence of the Kv1.3 protein is unclear. We, therefore, studied the effect of Kv1.3 inhibition on insulin sensitivity of wild-type, C57BL/6 mice. As shown herein, wild type mice that received a single injection of margatoxin (blocks Kv1.2 and Kv1.3, Mourre et al., 1999, J. Pharamcol. Exp. Ther. 291:943–952) 4 hours prior to study had lower fasting blood glucose compared to mice that were given phosphate buffered saline (PBS). Furthermore, toxin-treated mice exhibited a significantly lower blood glucose in response to insulin. It was then examined whether Kv1.3 inhibition could ameliorate the insulin insensitivity observed in mice with type II diabetes mellitus and obesity. Db/db mice carry a mutation in the leptin receptor leading to obesity, insulin resistance and hyperglycemia. As the mouse matures insulin levels begin to fall, resulting in moderately severe hyperglycemia. At about 8-weeks of age, db/db mice typically have blood glucose levels ranging from 300 to 350 mg/dl (Manchem et al., 2001, Diabetes 50:824–830). Inhibition of Kv1.3 by margatoxin resulted in a significantly greater fall in blood glucose of db/db mice receiving insulin compared to those given PBS and insulin. The difference in glucose levels was evident within 30 minutes and persisted for up to 4.5 hours. Although Margatoxin is a fairly specific and potent inhibitor of Kv1.3, it also blocks Kv1.2. It could, therefore, increase insulin sensitivity by blocking Kv1.2 channels. That hypothesis was tested by testing kaliotoxin, which inhibits both Kv1.3 (IC50=0.6 nM) and Kv1.1 (IC50=40 nM) but not Kv1.2. Animals treated with kaliotoxin and insulin had significantly lower blood glucose than those only receiving insulin. The ob/ob mouse (C57BL/6J background, Jackson Labs, Bar Harbor, Me.) carries a mutation in the leptin gene, and exhibits severe obesity, insulin resistance, hyperinsulinemia, and hyperglycemia. Ob/ob mice treated with a single injection of margatoxin were significantly more sensitive to insulin than mice receiving PBS, with a fall in blood glucose in response to insulin administration 50% greater in margatoxin-treated animals as compared to control mice. The difference in glucose level was evident within 30 minutes following the administration of insulin and persisted for at least 3 hours. These data provide further evidence in support of the notion that inhibition of Kv1.3 currents increases insulin sensitivity.

To investigate the mechanisms of increased insulin sensitivity in Kv1.3-deficient mice, the role of Kv1.3 on glucose uptake in skeletal muscle cells, one of the most important insulin-responsive tissues in the body, was examined. L6 cells express Kv1.3 and mediate insulin-sensitive glucose uptake primarily through the glucose transporter GLUT-4. They also express GLUT-1 and GLUT-3 and both can translocate to the plasma membrane and mediate insulin-independent glucose uptake (Hajduch et al., 1999, J. Biol. Chem 274:13563–13568). As shown herein, margatoxin causes a significant increase in phloretin-sensitive glucose uptake in L6 cells. The concentration of Margatoxin (53 nM) necessary for 1/2 maximal increase in glucose uptake is slightly higher than the Ki for Kv1.3 current (2–6 $\mu$M). A potential explanation for this discrepancy is the presence, in the L6 uptake buffer, of plasma proteins that can bind margatoxin. The effect of toxin on glucose uptake is additive to that of insulin, suggesting that activation of GLUT-1 and GLUT-3 may also contribute to the observed increase in glucose uptake and that GLUT-4 recruitment to the plasma membrane occurs via an insulin-independent process. Of note, membrane depolarization induced by high extracellular K increases glucose uptake by recruiting GLUT-4 from intracellular vesicles to the plasma membrane of H9c2 myotubes via a $Ca^{2+}$-dependent but P13-independent mechanism (Yu et al., 1999, Am J. Physiol 277:E259–E367). Since glucose transport is rate-controlling for glucose utilization in skeletal muscle (Cline et al., 1999, N. Engl. J. Med. 341:240–246), and it is likely that the enhanced glucose transport in muscle tissue is largely responsible for the apparent increased insulin sensitivity observed in Kv1.3 (−/−) mice. Without wishing to be bound by any particular theory, margatoxin may inhibit Kv1.3, depolarizes membrane potential, and facilitates the translocation of GLUT-1, GLUT-3 and GLUT-4.

The signaling cascade initiated by the binding of insulin to its receptor (IR) at the plasma membrane is complex and the subject of intense scrutiny. Insulin binds to IR and causes it to undergo autophosphorylation at tyrosine residues. Phosphorylated IR displays increased tyrosine kinase activity and in turn phophorylates a number of proteins including insulin receptor substrates (IRS). IRS are believed to recruit a variety of kinases such as P13-kinase and phosphatases containing Src homology 2 domains (SH2) that ultimately mediate the metabolic effect of insulin. Recent studies indicate that Kv1.3 might serve as substrate of IR. Kv1.3 channel activity is inhibited by tyrosine phosphorylation both in vivo and in vitro (Fadool et al., 2000, Neurophysiol 83:2332–2358; Bowlby et al., 1997, J. Gen Physiol 110:601–610). Kv1.3 inhibition could depolarize the cell membrane and modulate intracellular calcium and subsequent signaling events. It is noteworthy that membrane depolarization could affect glucose metabolism through of insulin-independent mechanisms. Muscle contraction and membrane depolarization achieved by high extracellular potassium appear to stimulate glucose uptake by recruiting GLUT4 to the plasma membrane through an insulin-independent pathway (Yu et al., 1999, Am J. Physiol 277:E259–E267). Serotonin increases skeletal muscle glucose uptake, independent of insulin, by facilitating GLUT-1, GLUT-3 and GLUT-4 translocation to the plasma membrane (Hajduch et al., 1999, J. Biol. Chem. 274:13563–13568).

Other Kv channels (Kv1.x and Kv2.x) channel, also regulate glucose homeostasis by controlling the membrane potential, and insulin secretion of the pancreatic β cells (MacDonald et al., 2001, Mol. Endocrinol. 15:1423–1435). The ATP-sensitive potassium channel ($K_{ATP}$) regulates membrane potential of pancreatic beta cells and modulates insulin secretion. Inhibition of KATP by sulfonylurea compounds depolarizes the cells and activates voltage-sensitive $Ca^{2+}$ channel leading to an increase in intracellular $Ca^{2+}$ concentration and a stimulation of insulin secretion. In addition to their effect on insulin secretion, these compounds can also increase insulin sensitivity in insulin-responsive tissues. $K_{ATP}$ deficient mice develop hypoglycemia and have a defect in glucagon secretion. In contrast to what is observed with KATP inhibition or deletion (Miki et al., 2001, Nat. Neurosci 4:507–512) Kv1.3 deficiency does not cause an increase in insulin secretion arid is not associated with abnormalities in glucagon secretion. Furthermore, since Kv1.3 is not expressed in the pancreas, its role in glucose homeostasis is distinct from that these other potassium channels.

Increased insulin sensitivity is occasionally observed as a side-effect of therapeutically useful compounds. For instance, fluxetine (Breum et al., 1995, Metabolism 44:1570–1576; Potter van Loon et al., 1992, Int. J. Obes. Rela. Metab. Disord. 16:S55–S61; Potter van Loon et al., 1992, Int. J. Obes. Rela. Metab,. Disord. 16:79–85) and verapamil (Dal Ponte et al., 1998, Metabolism 47:982–987) are known to increase insulin sensitivity at therapeutic dosages. The exact mechanisms mediating their effect on insulin sensitivity remain unknown. Interestingly, therapeutic levels of both fluxetine (Choi et al., 1999, Journal of Pharmacology & Experimental Therapeutics 291:1–6; Yeung et al., 1999, Br. J. Pharmacol 128:1609–1615) and verapamil (Madeja et al., 2000, Neuropharmacology 39:202–210; Robe et al., 2000, Br. J. Pharmacol 131:1275–1284) inhibit Kv1.3 activity, and it is conceivable that these drugs modulate insulin sensitivity through inhibition of Kv1.3 currents. In summary, the data disclosed herein demonstrate that Kv1.3 as an important molecule in glucose homeostasis and body weight regulation. Therefore, Kv1.3 and its signaling pathway can be used as a potential targets for the development of drugs useful in the management of diabetes and body weight control.

The data disclosed herein demonstrate that Kv1.3 is a key molecule in the signal transduction pathway for controlling food intake and weight. It has been postulated that insulin receptor in the brain plays an important role in the CNS control of energy homeostasis. Indeed, Bruning et al. showed that mice lacking neuronal insulin receptor have a 15% weight gain (Bruning et al., 2000, Science, 289: 2122–2125), suggesting that brain insulin signaling is involved in weight control. However, the exact signal pathway detailing the relevant insulin receptor substrates (IRS) remains unknown. Recently, Fadool et al. demonstrated that one of the IRS is Kv1.3. Its activity is down-regulated by insulin (Fadool et al., 2000, J. Neurophysiol. 83: 2332–2348), presumably through insulin receptor and subsequent tyrosine phosphorylation of Kv1.3. However, they did not suggest that Kv1.3 is involved in the signal transduction pathway for food intake and weight control. By analyzing the phenotype of Kv1.3 knockout mice, the data disclosed herein demonstrate that Kv1.3 participates in energy homeostasis. Indeed, loss-of-function leads to a reduction in food intake and lower body weight. These findings suggest a novel therapeutic approach for the treatment of obesity: inhibition of Kv1.3 and its subsequent signal transduction. Loss of Kv1.3 function in unlikely to cause significant adverse effects. Indeed, the Kv1.3 knockout mice do not exhibit any discernable phenotypical differences other than weight changes. Interestingly, although Kv1.3 is expressed in T lymphocytes and in the CNS, no immune defect or brain development abnormality was detected in knock-out mice lacking the gene.

The present invention also suggests several avenues for treating obesity by manipulating IR-Kv1.3 pathway. For example, when insulin binds to IR, IR kinase phosphorylates tyrosine residues in Kv1.3, resulting in decreased channel activity, thus, through decreased Kv1.3 activity, causes decreased food intake and body weight reduction.

Chemical compounds can be used as weight control medication to activate IR kinase. Conversely, inhibitors of the appropriate phosphatase will keep Kv1.3 in a phosphorylated state, thereby achieving the desired weight loss effect. Inhibition of Kv1.3 activity can also be used to increase insulin sensitivity and can be used as a therapeutic modality for diabetes.

In addition, the reduction of body fat stores in domestic animals is also of considerable economic benefit to man, since animals supply a major portion of man's diet, and the animal fat may end up as de novo fat deposits with resulting adverse effects on health. Thus, Kv1.3 and IR-Kv1.3 pathways can be used as targets to produce leaner animals for human consumption.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method for inducing weight loss in an animal, said method comprising administering to an animal a voltage-gated potassium channel Kv1.3 inhibiting amount of a Kv1.3 inhibitor, wherein said Kv1.3 inhibitor is a chemical compound, wherein said chemical compound is a short scorpion toxin, wherein said short scorpion toxin is margatoxin thereby inducing weight loss in said animal.

2. A method for decreasing body fat in animal, said method comprising administering a Kv1.3 inhibiting amount of a Kv1.3 inhibitor to said animal, wherein said inhibitor is margatoxin, thereby decreasing body fat in said animal.

3. The method of claim 2, wherein said animal is selected from the group consisting of a bird, a rodent, and a mammal, and further wherein said mammal is selected from the group consisting of a cow, a pig, a sheep, a buffalo, a beefalo, a bison, a deer, a goat, and a human.

4. A method for increasing insulin sensitivity in an animal, said method comprising administering a Kv1.3 inhibiting amount of a Kv1.3 inhibitor to an animal, wherein said inhibitor is margatoxin, thereby increasing insulin sensitivity in said animal.

5. A method for decreasing food intake in an animal, said method comprising administering a Kv1.3 inhibiting amount of a Kv1.3 inhibitor to an animal, wherein said inhibitor is margatoxin, thereby decreasing food intake in said animal.

6. A method for affecting appetite in an animal, said method comprising administering a Kv1.3 inhibiting amount of a Kv1.3 inhibitor to an animal, wherein said inhibitor is margatoxin, thereby affecting appetite in said animal.

7. A method for treating obesity in an animal, said method comprising administering a Kv1.3 inhibiting amount of a Kv1.3 inhibitor to an animal, wherein said inhibitor is margatoxin, thereby treating obesity in said animal.

8. A method for preventing obesity in a animal, said method comprising administering a Kv1.3 inhibiting amount of a Kv1.3 inhibitor to an animal, wherein said inhibitor is margatoxin, thereby preventing obesity in said animal.

9. A method for treating a glucose-metabolism disease or disorder in an animal, said method comprising administering a Kv1.3 inhibiting amount of a Kv1.3 inhibitor to an animal, wherein said inhibitor is margatoxin, thereby treating a glucose-metabolism disorder in said animal.

10. The method of claim 9, wherein said glucose-metabolism disease or disorder is selected from the group consisting of obesity, diabetes, insulin resistance, glucose intolerance, hyerinsulinemia, Syndrome X, hypercholesterolemia, hyperlipoproteinemia, hypertriglyceridemia, atherosclerosis, and diabetic renal disease.

11. A method for affecting physical activity in an animal, said method comprising administering a Kv1.3 inhibiting amount of a Kv1.3 inhibitor to an animal, wherein said inhibitor is margatoxin, thereby affecting physical activity in said animal.

12. A method for affecting metabolic rate in an animal, said method comprising administering a Kv1.3 inhibiting amount of a Kv1.3 inhibitor to an animal, wherein said inhibitor is margatoxin, thereby affecting metabolic rate in said animal.

* * * * *

UNITED STATES PATENT AND TRADEMARK OFFICE
CERTIFICATE OF CORRECTION

PATENT NO. : 6,861,405 B2
DATED : March 1, 2005
INVENTOR(S) : Gary Desir et al.

It is certified that error appears in the above-identified patent and that said Letters Patent is hereby corrected as shown below:

Title page,
Item [75], Inventors, delete "Pandelakis A. Koni, Martinez, GA (US); Leonard Kaczmarek, Guilford, CT (US); Richard A. Flavell, Guilford, CT (US)"

Signed and Sealed this

Twenty-fourth Day of May, 2005

JON W. DUDAS
*Director of the United States Patent and Trademark Office*

SEQUENCE LISTING

```
<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
<223> OTHER INFORMATION: 5' Kv1.3 PCR Primer

<400> SEQUENCE: 1
atacttcgac ccgctccgca atga                                          24

<210> SEQ ID NO 2
<211> LENGTH: 24
<212> TYPE: DNA
<213> ORGANISM: Artificial Sequence
<220> FEATURE:
<223> OTHER INFORMATION: 3' Kv1.3 PCR Primer

<400> SEQUENCE: 2
gcagaagatg acaatggaga tgag                                          24
```